(12) United States Patent
Plakogiannis et al.

(10) Patent No.: US 10,500,196 B2
(45) Date of Patent: Dec. 10, 2019

(54) TRANSDERMAL AND/OR TOPICAL DELIVERY SYSTEMS COMPOSED OF DOXYLAMINE SUCCINATE AND PYRIDOXINE HYDROCHLORIDE IN COMBINATION, OR ALONE

(71) Applicant: Aequus Pharmaceuticals Inc., Vancouver (CA)

(72) Inventors: Fotios M. Plakogiannis, Whitestone, NY (US); Donald McAfee, Pt. Roberts, WA (US); Tamanna Lather, Jersey City, NJ (US); Marina Borovinskaya, East Brunswick, NJ (US)

(73) Assignee: Alpha To Omega Pharmaceutical Consultants, Inc., Whitestone, NY (US)

( * ) Notice: Subject to any disclaimer, the term of this patent is extended or adjusted under 35 U.S.C. 154(b) by 249 days.

(21) Appl. No.: 15/228,382

(22) Filed: Aug. 4, 2016

(65) Prior Publication Data

US 2017/0049759 A1 Feb. 23, 2017

Related U.S. Application Data

(60) Provisional application No. 62/205,941, filed on Aug. 17, 2015.

(51) Int. Cl.
| | |
|---|---|
| *A61K 31/4415* | (2006.01) |
| *A61K 31/435* | (2006.01) |
| *A61K 9/00* | (2006.01) |
| *A61K 31/4402* | (2006.01) |
| *A61K 9/06* | (2006.01) |
| *A61K 47/10* | (2017.01) |
| *A61K 47/24* | (2006.01) |
| *A61K 47/38* | (2006.01) |

(52) U.S. Cl.
CPC ........ *A61K 31/4415* (2013.01); *A61K 9/0014* (2013.01); *A61K 9/06* (2013.01); *A61K 31/4402* (2013.01); *A61K 47/10* (2013.01); *A61K 47/24* (2013.01); *A61K 47/38* (2013.01)

(58) Field of Classification Search
CPC ............ A61K 31/4402; A61K 31/4415; A61K 31/435
USPC ....................................................... 514/357
See application file for complete search history.

(56) References Cited

U.S. PATENT DOCUMENTS

| | | |
|---|---|---|
| 6,340,695 B1 | 1/2002 | Gervais |
| 7,560,122 B2 | 7/2009 | Gervals et al. |
| 9,089,489 B2 | 7/2015 | Vranderick |
| 2005/0004181 A1* | 1/2005 | Reeve .................... A61K 31/44 514/350 |
| 2013/0184243 A1* | 7/2013 | Alonso ................ A61K 31/131 514/171 |
| 2014/0335176 A1 | 11/2014 | Mandaogade |

FOREIGN PATENT DOCUMENTS

| | | |
|---|---|---|
| CA | 2117265 C | 4/1993 |
| CA | 2432945 A1 | 9/2003 |
| CA | 2479018 A1 | 10/2003 |
| CA | 2521423 A1 | 10/2004 |
| CA | 2529860 A1 | 12/2004 |
| CA | 2606724 A1 | 11/2006 |
| CA | 2882870 A1 | 2/2014 |
| CA | 2897685 A1 | 7/2014 |
| CN | 103432126 A | 12/2013 |
| IE | 20030484 A1 | 1/2004 |
| WO | WO-2014031958 | * 2/2014 |

OTHER PUBLICATIONS

Paudel et al. ("Challenges and opportunities in dermal/transdermal delivery." Ther Deliv. Jul. 2010; 1(1): 109-131).*
Anonymous: "Women's Health Compounding Ideas", 3 pages, Created Apr. 17, 2013, Retrieved on Oct. 25, 2016 at http://www.medicineshoppe.com/~/media/images/sites/the%20medicine%20shoppe/0279/womenshealth%20compounding%20ideas.ashx.
International Search Report for PCT/IB2016/054722 dated Nov. 24, 2016.
Diclectin® Product Monograph doxylamine succinate and pyridoxine hydrochloride delayed release tablets (10 mg/10 mg) Antinauseant against Nausea and Vomiting of Pregnancy. Duchesnay Inc. Feb. 15, 2017.
Predicting Chemical Uptake Into Skin. Richard H. Guy. University of Bath. Downloaded Oct. 29, 2018. https://www.google.com/url?sa=t&rct=j&q=&esrc=s&source=web&cd=1&ved=2ahUKEwjl-rH57lPfAhXilOAKHb94BFIQFjAAegQIBxAC&url=https%3A%2F%2Fwww.soci.org%2F-%2Fmedia%2FFiles%2FConference-Downloads%2F2012%2FUptake-Across-the-Leaf-Cuticle-and-Skin-Nov-2012%2FRichard_Guy_Presentation.ashx%3Fla%3Den&usg=AOvVaw2Nglwl3Y2lCtkNSFFtOStl.

(Continued)

Primary Examiner — Rachael E Bredefeld
Assistant Examiner — Chris E Simmons
(74) Attorney, Agent, or Firm — Caesar Rivise, PC

(57) ABSTRACT

Pharmaceutical compositions for simultaneous transdermal delivery of Doxylamine and Pyridoxine comprising Doxylamine or its salts, Pyridoxine or its salts or its active metabolites and a vehicle system wherein pharmaceutical compositions are liquid formulations, semisolid formulations and polymer matrices. Further pharmaceutical compositions can be incorporated into transdermal delivery systems or transdermal patches. The invention provides a method for treatment of nausea and vomiting in general, and for pregnant women in particular by continuous and simultaneous transdermal delivery of Doxylamine and Pyridoxine. This is to be accomplished through topical application of pharmaceutical compositions or by application of a transdermal delivery system or transdermal patch to the surface of the skin wherein the duration of application is once in a day, once every two days, once every three days, once every four days, once every five days, once every six days, or once in a week.

10 Claims, 3 Drawing Sheets

(56) References Cited

OTHER PUBLICATIONS

Chandrashekar, NS. et al. Physicochemical and Pharmacokinetic Parameters in Drug Selection and Loading for Transdermal Drug Delivery. Indian J Pharm Sci. Jan.-Feb. 2008; 70(1): 94-96.
Venter, JP. et al. A comparative study of an in situ adapted diffusion cell and an in vitro Franz diffusion cell method for transdermal absorption of doxylamine. Eur J Pharm Sci. May 2001;13(2):169-77.
European Search Report dated Apr. 8, 2019, for EP-20160836711.
FDA Letter dated Apr. 20, 2018, Reference ID: 4252068. PIND 138162.
Pastore, MN, et al. Br J Pharmacol., May 2015; 172(9):2179-209.
Van Buskirk GA. et al. Passive transdermal systems whitepaper incorporating current chemistry, manufacturing and controls (CMC) development principles. AAPS PharmSciTech. Mar. 2012; 13(1):218-30.
Regulatory, TOX and Safety Overview. Lauroglycol™ FCC (Code: 3219); Lauroglycol™ 90 (Code: 3244); Gattefossé SAS, Dec. 21, 2011.

\* cited by examiner

TRANSDERMAL AND/OR TOPICAL DELIVERY SYSTEMS COMPOSED OF DOXYLAMINE SUCCINATE AND PYRIDOXINE HYDROCHLORIDE IN COMBINATION, OR ALONE

This application claims benefit under 35 U.S.C. § 119(e) of U.S. Provisional Patent Application No. 62/205,941, filed Aug. 17, 2015, the contents of which are incorporated in their entirety herein.

BACKGROUND OF THE INVENTION

1. Field of Invention

The present invention relates to the field of simultaneous transdermal delivery of Doxylamine or its various salts and Pyridoxine or its various salts and active metabolites from Novel pharmaceutical compositions. The pharmaceutical compositions have simultaneous in vitro release profile of Doxylamine and Pyridoxine from 1-3 days and 1-7 days. In particular, the pharmaceutical compositions of the present invention includes liquid formulations, semisolid formulations, and polymer matrix formulations comprised of Doxylamine, Pyridoxine and a vehicle system. Surprisingly, from a liquid formulation the average in vitro flux for Doxylamine Succinate and Pyridoxine Hydrochloride is almost the same for any period from 24 to 168 hours. Furthermore, surprisingly, from semisolid formulations the average in vivo flux over seven days is the same for Doxylamine Succinate and Pyridoxine Hydrochloride.

2. Description of Related Art

Nausea and Vomiting during Pregnancy (NVP) occurs in approximately 70% of pregnant women, making it the most common ailment during pregnancy[1]. Severity and occurrence of NVP symptoms are variable among women. Severity of symptoms like gagging, nausea, vomiting, retching can vary from mild to severe. A spectrum of symptoms occur from morning throughout the day and even into the night. Generally symptoms of NVP onset between 4-9 weeks, get severe between 7-12 weeks and then tapers down from the 12th week. However, 15% of pregnant women experience NVP symptoms for up to 20 weeks, and less than 10% experience it throughout their pregnancy[4,2]. NVP affects women's quality and comfort of life during pregnancy[2]. A study was conducted with 160 pregnant women and reported that 74% women had nausea, of which 80% reported nausea all day long[3]. The initial approach in managing NVP is to make dietary changes including the avoidance of trigger odors and foods. If that approach does not resolve symptoms on its own, guidance recommends the addition of pharmacotherapy[5].

DICLEGIS® is the only US FDA approved drug for the treatment of NVP. It is a delayed release oral tablet, a fixed dose combination of 10 mg Doxylamine Succinate and 10 mg Pyridoxine Hydrochloride[6].

A number of shortcomings are associated with the commercially available oral tablet DICLEGIS both in dosage regimen and pharmacokinetic profile. The first challenge is the dose regimen as stated in FDA DICLEGIS label to "take two tablets daily at bedtime and if symptoms are not adequately controlled, the dose can be increased to a maximum recommended dose of four tablets daily (one in the morning, one mid-afternoon and two at bedtime)"[6]. This multiple dose regimen is inconvenient for pregnant women, particularly for those who experience vomiting within a short time after dosing (i.e., within one hour) and have uncertainty as to whether taking another dose would be permissible. The second challenge is taking the dose on an empty stomach because the absorption of Doxylamine Succinate and Pyridoxine Hydrochloride gets delayed when administered with food. Moreover, it is reported that the bioavailability of pyridoxine reduces with food[6]. Hence forth for treatment of NVP, there is a need for an improved drug delivery system which can reduce dosing frequency of Doxylamine and Pyridoxine, and provide a sustained release for a prolonged therapeutic effect overcoming the problems associated with the administration of delayed release DICLEGIS tablet.

Transdermal drug delivery is a delivery of drug through, for example, an intact skin surface. By topical application of transdermal composition or transdermal delivery system to the skin surface, such as intact skin, drug is continuously delivered from a transdermal delivery system through the skin (via transcellular, intercellular and transappendageal routes) to achieve a systemic effect.

Transdermal delivery of Doxylamine Succinate and Pyridoxine Hydrochloride can address the challenges associated with the commercially available oral tablet (DICLEGIS) including dosage regimen and pharmacokinetic profile. With respect to dosage regimen, the dosing frequency can be reduced and simplified by applying a pharmaceutical composition or transdermal delivery system to, for example, intact skin which can provide continuous or sustained systemic delivery of Doxylamine Succinate and Pyridoxine Hydrochloride throughout the duration of application. By transdermal delivery, Doxylamine Succinate and Pyridoxine Hydrochloride reaches systemic circulation through the skin. Thus, absorption of both drugs is not affected by a fed or fasted state, unlike an oral tablet which should be taken on an empty stomach. Depending upon the severity of symptoms, the duration of topical application or transdermal delivery of the drugs can be once a day, once every two days, once every three days, once every four days, once every five days, once every six days, once in a week, or possibly even once every 15 days. Therefore transdermal delivery of Doxylamine Succinate and Pyridoxine Hydrochloride can improve the quality of life of those suffering from nausea and vomiting with a simplified and convenient therapeutic regimen.

There are patents known in the art for oral delivery of Doxylamine Succinate and Pyridoxine Hydrochloride. For example, U.S. Pat. No. 6,340,695B1 discloses an enterically coated rapid onset oral formulation comprising Doxylamine Succinate and Pyridoxine Hydrochloride. US Patent Application Number 20140335176A1 discloses a disintegrant free delayed release oral composition of Doxylamine Succinate and Pyridoxine Hydrochloride. U.S. Pat. No. 9,089,489B2 discloses and states that "a dual release oral dosage system comprising immediate release component and delayed release component". The prior art does not describe or inform on Transdermal Delivery of Doxylamine Succinate and Pyridoxine Hydrochloride, nor does it inform on techniques which can reduce the dosing frequency to at least once in three days, to at least once in seven days.

The invention provides a transdermal pharmaceutical composition in a liquid formulation comprising: Doxylamine as a free base or any of its salts; Pyridoxine as a free base or any of its salts or its active metabolites; and a vehicle system wherein the vehicle system comprises excipients selected from the group consisting of solvents, enhancers, pH adjusting agents, and combinations thereof.

The invention provides a transdermal pharmaceutical composition wherein: Doxylamine is present in an amount selected from the group consisting of between 0.5-49 wt %, between 2-30 wt %, between 5-20 wt %; Pyridoxine is present in an amount selected from the group consisting of between 0.5-49 wt %, between 2-30 wt %, between 5-20 wt %, and wherein the vehicle system is present in an amount selected from the group consisting of between 2-99 wt %, preferably between 40-96 wt %, and between 60-90 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition, wherein nausea or nausea and vomiting is treated and/or prevented in the patient.

The invention provides a method, wherein the application is to skin, such as intact skin, and wherein frequency of topical application is selected from the group consisting of once in a day, once in two days, once in three days, once in four days, once in five days, once in six days, days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition wherein NVP is treated and/or prevented in the patient.

The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a liquid formulation comprising: Doxylamine as a free base or any of its salts; and a vehicle system wherein the vehicle system comprises excipients selected from the group consisting of solvents, enhancers, pH adjusting agents, and combinations thereof.

The invention provides a transdermal pharmaceutical composition wherein: Doxylamine is present in an amount selected from the group consisting of between 0.5-80 wt %, between 2-30 wt %, between 5-20 wt %, and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition, wherein nausea or nausea and vomiting is treated and/or prevented in the patient.

The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition wherein NVP is treated and/or prevented in the patient.

The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a liquid formulation comprising: pyridoxine as a free base or any of its salts or its active metabolites; and a vehicle system wherein the vehicle system comprises excipients selected from the group consisting of solvents, enhancers, pH adjusting agents, and combinations thereof.

The invention provides a transdermal pharmaceutical composition wherein: Pyridoxine is present in an amount selected from the group consisting of between 0.5-80 wt %, between 2-30 wt %, and between 5-20 wt %, wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition, wherein nausea or nausea and vomiting is treated and/or prevented in the patient.

The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition, wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a semisolid formulation comprising: Doxylamine as a free base or any of its salts; Pyridoxine as a free base or any of its salts or its active metabolites; and a vehicle system wherein the vehicle system comprises excipients selected from the group consisting of solvents, enhancers, polymers or gelling agents or thickening agents, pH adjusting agents, and combinations thereof. The invention provides a transdermal pharmaceutical composition wherein: Doxylamine is present in an amount selected from the group consisting of between 0.5-49 wt %, between 2-30 wt %, and between 5-20 wt %; Pyridoxine is present in an amount selected from the group consisting of between 0.5-49 wt %, between 2-30 wt %, and between 5-20 wt %; and wherein the vehicle system is present in an amount selected from the group consisting of between 2-99 wt %, between 40-96 wt %, and between 60-90 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition, wherein nausea or nausea and vomiting is treated and/or prevented in the patient.

The invention provides a method, wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition, wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition as a semisolid formulation comprising: Doxylamine as a free base or any of its salts; and a vehicle system wherein the vehicle system comprises excipients selected from the group consisting of solvents, enhancers, polymers or gelling agents or thickening agents, pH adjusting agents, and combinations thereof. The invention provides a transdermal pharmaceutical composition wherein: Doxylamine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition, wherein nausea or nausea and vomiting is treated and/or prevented in the patient.

The invention provides a method wherein the application is to intact skin and wherein frequency of topical application is selected from the group consisting of once in a day, once in two days, once in three days, once in four days, once in five days, once in six days, once in a week, once in ten days, and once in fifteen days. The invention provides a method of treating and/or preventing nausea and vomiting in pregnancy (NVP) in a patient comprising: selecting a patient in need of treating and/or preventing NVP; administering to the patient the transdermal pharmaceutical composition, wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a semisolid formulation comprising: Pyridoxine as a free base or any of its salts or its active metabolites; and a vehicle system wherein the vehicle system comprises excipients selected from the group consisting of solvents, enhancers, polymers or gelling agents or thickening agents, pH adjusting agents, and combinations thereof.

The invention provides a transdermal pharmaceutical composition wherein: Pyridoxine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition, wherein nausea or nausea and vomiting is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition, wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a polymer matrix comprising: Doxylamine as a free base or any of its salts; Pyridoxine as a free base or any of its salts or its active metabolites; and a vehicle system wherein the vehicle system comprises excipients selected from the group consisting of solvents, enhancers, plasticizers, polymers, pH adjusting agents, and combinations thereof. The invention provides a transdermal pharmaceutical composition wherein: Doxylamine is present in an amount selected from the group consisting of between 0.5-49 wt %, between 2-30 wt %, and between 5-20 wt %; Pyridoxine is present in an amount selected from the group consisting of between 0.5-49 wt %, between 2-30 wt %, and between 5-20 wt %; and wherein the vehicle system is present in an amount selected from the group consisting of between 2-99 wt %, between 40-96 wt %, and between 60-90 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition wherein nausea or nausea and vomiting is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a polymer matrix comprising: Doxylamine as a free base or any of its salts; and a vehicle system wherein the vehicle system comprises excipients selected from the group consisting of solvents, enhancers, plasticizers, polymers, pH adjusting agents, and combinations thereof. The invention provides a transdermal pharmaceutical composition wherein: Doxylamine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition wherein nausea or nausea and vomiting is treated and/or prevented in the patient.

The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a polymer matrix comprising: Pyridoxine as a free base or any of its salts or its active metabolites; and a vehicle system wherein the vehicle system comprises excipients selected from the group consisting of solvents, enhancers, plasticizers, polymers, pH adjusting agents, and combinations thereof. The invention provides a transdermal pharmaceutical composition wherein: Pyridoxine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition wherein nausea or nausea and vomiting is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition wherein NVP is treated and/or prevented in the patient. The invention provides a method wherein the application is to intact skin and wherein frequency of topical application is selected from the group consisting of once in a day, once in two days, once in three days, once in four days, once in five days, once in six days, once in a week, once in ten days, and once in fifteen days.

The invention provides doxylamine and/or pyridoxine for use in the preparation of a medicament for use in treating and/or preventing nausea and vomiting in pregnancy (NVP). The invention provides doxylamine and/or pyridoxine for use in the preparation of a medicament for use in treating and/or preventing nausea and vomiting.

The invention provides method for treating or preventing a disease or condition in a patient, wherein the disease or condition is selected from the group consisting of nausea and vomiting or NVP, and combinations thereof, wherein said method comprises: selecting a patient in need of treating or preventing said disease or condition; administering to the patient the composition of the invention in a therapeutically effective amount, thereby treating and/or preventing the condition.

All references cited herein are incorporated herein by reference in their entireties.

BRIEF SUMMARY OF THE INVENTION

The Invention provides the pharmaceutical compositions for transdermal delivery of Doxylamine and its various salts and/or Pyridoxine and its various salts, and its active metabolites wherein pharmaceutical compositions provide simultaneous transdermal delivery of Doxylamine Succinate and Pyridoxine Hydrochloride are preferred. Embodiments and aspects described below are exemplary and illustrating without limiting in scope.

In one embodiment, the invention provides pharmaceutical compositions as Liquid formulation for transdermal delivery of Doxylamine and/or Pyridoxine. In one aspect a liquid formulation comprised of Doxylamine Succinate, Pyridoxine Hydrochloride and Vehicle system wherein, Doxylamine Succinate is present in an amount between 0.5-49 wt %, Pyridoxine Hydrochloride is present in an amount between 0.5-49 wt % and vehicle system is present in an amount between 2-99 wt %. In another aspect, a liquid formulation comprised of Doxylamine Succinate and Vehicle system wherein, Doxylamine Succinate is present in an amount between 0.5-80 wt %, and Vehicle system is present in an amount between 20-99.5 wt %. In yet another aspect, a liquid formulation comprised of Pyridoxine Hydrochloride and Vehicle system wherein, Pyridoxine Hydrochloride is present in an amount between 0.5-80 wt %, and Vehicle system is present in an amount between 20-99.5 wt %. The liquid formulation comprising Doxylamine Succinate, Pyridoxine Hydrochloride and vehicle system is preferred.

The invention further provides a vehicle system for one embodiment, comprising: solvents, enhancers, and, if required, pH adjusting agents either alone or in combinations thereof, wherein solvents suitable for use include glycol, polyhydric alcohol, alcohol, sulfoxide, pyrrolidone, mineral oil, vegetable oil, acids, glycol ether, polar solvent, surfactant, emulsifying agent, derivatives of glycols, skin irritation reducing agents, emollient, humectant either alone or in combinations thereof.

Enhancers suitable for use include surfactants, fatty acids, alcohol, fatty alcohols and glycol, esters, fatty acid esters and fatty alcohol esters, esters of long chain fatty acids with methyl, ethyl, isopropyl alcohols, esters of fatty alcohols with acetic acid, lactic acid as well as oleic acid, diethanolamine, essential oils, terpene and terpenoids, amides, urea, polyoxyethylene fatty alcohol ethers, polyoxyethylene fatty acid esters, sulfoxide, ether alcohol, pyrrolidones, transcarbam, capsaicin derivatives, dimethylamino acid esters, peptides, iminosulfuranes, dicarboxylic acid esters, nanocarriers, triglycerides, hydrocarbons, phospholipids either alone or in combinations thereof.

One aspect of the invention further provides an exemplary liquid formulation comprising about 0.5-45 wt % Doxylamine Succinate, 0.5-45 wt % Pyridoxine Hydrochloride, 0.5-70 wt % dimethylsulfoxide, 0.5-50 wt % ethanol, 0.5-80 wt % dipropylene glycol, 0.5-80 wt % diethylene glycol monoethyl ether, 0.5-50 wt % propylene glycol monolaurate type (II), 0.5-95 wt % water, pH between 3-8.

Another aspect of the invention further provides an exemplary liquid formulation comprising about 0.5-45 wt % Doxylamine Succinate, 0.5-45 wt % Pyridoxine Hydrochloride, 0.5-70 wt % dimethylsulfoxide, 0.5-80 wt % hexylene glycol, 0.5-80 wt % propylene glycol, 0.5-80 wt % polyethylene glycol 400, 0.5-80 wt % dipropylene glycol, 0.5-80 wt % diethylene glycol monoethyl ether, 0.5-50 wt % propylene glycol monolaurate type (II), 0.5-94 wt % water, pH between 3-8.

Another aspect of the invention provides an exemplary liquid formulation comprising about 0.5-45 wt % Doxylamine Succinate, 0.5-70 wt % dimethylsulfoxide, 0.5-50 wt % ethanol, 0.5-80 wt % dipropylene glycol, 0.5-80 wt %, diethylene glycol monoethyl ether, 0.5-50% wt propylene glycol monolaurate type (II), 0.5-95% wt water, hydrochloric acid and/or sodium hydroxide to adjust pH between 3-8.

Yet another aspect of the invention provides an exemplary liquid formulation comprising about 0.5-45 wt % Pyridoxine Hydrochloride, 0.5-70 wt % dimethylsulfoxide, 0.5-50 wt % ethanol, 0.5-80 wt % dipropylene glycol, 0.5-80 wt % diethylene glycol monoethyl ether, 0.5-50 wt % propylene glycol monolaurate type (II), 0.5-95 wt % water, hydrochloric acid and/or sodium hydroxide to adjust pH between 3-8.

In another embodiment, the invention provides pharmaceutical compositions as a semisolid formulation for transdermal delivery of Doxylamine and/or Pyridoxine.

One aspect of the semisolid formulation comprises Doxylamine Succinate, Pyridoxine Hydrochloride and a Vehicle system wherein, Doxylamine Succinate is present in an amount between 0.5-49 wt %, Pyridoxine Hydrochloride is present in an amount between 0.5-49 wt %, Vehicle system is present in an amount between 2-99 wt %. In another aspect, a semisolid formulation comprising Doxylamine Succinate and a Vehicle system wherein, Doxylamine Succinate is present in an amount between 0.5-80 wt %, Vehicle system is present in an amount between 20-99.5 wt %. In yet another aspect, a semisolid formulation comprising Pyridoxine Hydrochloride and a Vehicle system wherein, Pyridoxine Hydrochloride is present in an amount between 0.5-80 wt %, Vehicle system is present in an amount between 20-99.5 wt %. The semisolid formulation comprising Doxylamine Succinate, Pyridoxine Hydrochloride and vehicle system is preferred.

The invention further provides a vehicle system for semisolid formulation, comprising: solvents, enhancers, polymers or thickening agents or gelling agents or suspending agents, if required pH adjusting agents either alone or in combinations thereof, wherein solvents suitable for use include sulfoxides, glycol, polyhydric alcohol, alcohol, pyrrolidone, mineral oil, vegetable oil, acids, glycol ether, polar solvent, surfactant, emulsifying agent, derivatives of glycols, skin irritation reducing agents, emollient, humectant either alone or in combinations thereof.

Enhancers suitable for use include surfactants, fatty acids, alcohol, fatty alcohols and glycol, esters, fatty acid esters and fatty alcohol esters, esters of long chain fatty acids with methyl, ethyl, isopropyl alcohols, esters of fatty alcohols with acetic acid, lactic acid as well as oleic acid, diethanolamine, essential oils, terpene and terpenoids, amides, urea, polyoxyethylene fatty alcohol ethers, polyoxyethylene fatty acid esters, sulfoxide, ether alcohol, pyrrolidones, transcarbam, capsaicin derivatives, dimethylamino acid esters, peptides, iminosulfuranes, dicarboxylic acid esters, nanocarriers, triglycerides, hydrocarbons, phospholipids either alone or in combinations thereof.

Polymers or thickening agents or gelling agents or suspending agents suitable for use include cellulose and its derivatives, synthetic polymers and its derivatives, clays, silicates, all water swellable polymers, organic solvent swellable polymers, natural polymers, polysaccharides and its derivatives, resins, silicon dioxide, polyethylene and its co-polymers etc, polyvinyl alcohol, polyacrylamide, polyvinylpyrrolidone homopolymer and polyvinyl pyrrolidone copolymers, acrylic acid its ester, polyacrylate copolymers, suspending agents, dispersing agents either alone or in combinations thereof. Without limiting in scope the semisolid formulation can be in the dosage form of an ointment, gel, cream, emulsion, or liposome.

One aspect of the invention further provides an exemplary semisolid formulation comprising about 0.5-45 wt % Doxylamine Succinate, 0.5-45 wt % Pyridoxine Hydrochloride, 1-70 wt % dimethylsulfoxide, 0.5-80 wt % hexylene glycol, 0.5-80 wt % diethylene glycol monoethyl ether, 0.5-50 wt % propylene glycol monolaurate type (II), 0.5-95 wt % water, 0.25-50 wt % hydroxypropyl cellulose HF, pH between 3-8.

Another aspect of the invention further provides an exemplary semisolid formulation comprising about 0.5-45 wt % Doxylamine Succinate, 0.5-45 wt % Pyridoxine Hydrochloride, 1-70 wt % dimethylsulfoxide, 0.5-80 wt % hexylene glycol, 0.5-80 wt % diethylene glycol monoethyl ether, 0.5-80 wt % glycerine, 0.5-50 wt % propylene glycol monolaurate type (II), 0.5-94 wt % water, 0.25-50 wt % hydroxypropyl cellulose HF, pH between 3-8.

Another aspect of the invention further provides an exemplary semisolid formulation comprising about 0.5-45 wt % Doxylamine Succinate, 1-70 wt % dimethylsulfoxide, 0.5-80 wt % hexylene glycol, 0.5-80 wt % diethylene glycol monoethyl ether, 0.5-50 wt % propylene glycol monolaurate type (II), 0.5-95 wt % water, 0.25-50 wt % hydroxypropyl cellulose HF, hydrochloric acid and/or sodium hydroxide to adjust pH between 3-8.

In yet another aspect the invention further provides an exemplary semisolid formulation comprising about 0.5-45 wt % Pyridoxine Hydrochloride, 1-70 wt % dimethylsulfoxide, 0.5-80 wt % hexylene glycol, 0.5-80 wt % diethylene glycol monoethyl ether, 0.5-50 wt % propylene glycol monolaurate type (II), 0.5-95 wt % water, 0.25-50 wt % hydroxypropyl cellulose HF, hydrochloric acid and/or sodium hydroxide to adjust pH between 3-8.

In yet another embodiment, the invention provides a pharmaceutical composition as a polymer matrix for transdermal delivery of Doxylamine and Pyridoxine. In one aspect a polymer matrix comprised of Doxylamine Succinate, Pyridoxine Hydrochloride and Vehicle system wherein, Doxylamine Succinate is present in an amount between 0.5-49 wt %, Pyridoxine Hydrochloride is present in an amount between 0.5-49 wt %, Vehicle system is present in an amount between 2-99 wt %.

The invention further provides a vehicle system for polymer matrix, comprising: solvents, plasticizers, enhancers, polymers, if required pH adjusting agents, either alone or in combinations thereof, wherein solvents suitable for use includes such as volatile solvents, glycol, polyhydric alcohol, alcohol, sulfoxide, pyrrolidone, mineral oil, vegetable oil, acids, glycol ether, polar solvents, skin irritation reducing agents, humectants, emollients either alone in combinations thereof.

Enhancers suitable for use include surfactants, pyrrolidone, amide, sulfoxide, fatty acids, alcohol, fatty alcohol and glycol, ethers, urea, polyoxyethylene fatty, ether alcohol, diethanolamine, essential oils, terpene, esters, polyoxyethylene fatty acid esters, esters of fatty alcohols, esters of long chain fatty acids with methyl, ethyl or isopropyl alcohol, esters of fatty alcohols with acetic acid, lactic acid, as well as oleic acid, dicarboxylic acid esters, nanocarriers, transcarbam, capsaicin derivatives, peptides, iminosulfuranes, triglycerides, hydrocarbons, phospholipids either alone or in combinations thereof.

Polymers suitable for use include cellulose and its derivatives, synthetic polymers and its derivatives such as without any limitation to carboxyvinyl polymers or carbomers, clays, all water swellable polymers, organic solvent swellable polymers, natural polymers, polysaccharides and its derivatives, resins, silicon dioxide, polyethylene and its co-polymers etc, polyvinyl alcohol, polyacrylamide, polyacrylamide, polyvinylpyrrolidone homopolymer and polyvinyl pyrrolidone copolymers, acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, pressure sensitive adhesives based on silicone, acrylic copolymer adhesives, hot melt adhesive either alone or in combinations thereof.

Plasticizers suitable for use include glycerol and its esters, phosphate esters, glycol derivatives, sugar alcohols, mineral oil, sebacic acid esters, azelate, citric acid esters, tartaric acid esters, adipate, phthalic acid esters, triacetin, oleic acid esters either alone or in combinations thereof.

In one aspect invention further provides an exemplary polymer matrix of the invention further comprising about 0.5-45 wt % Doxylamine Succinate, 0.5-45 wt % Pyridoxine Hydrochloride, 1-50 wt % dimethylsulfoxide, 0.5-50 wt % glycerine, 0.5-50 wt % diethylene glycol monoethyl ether, 0.5-50 wt % propylene glycol monolaurate type (II), 0.5-70 wt % bentonite, 0.5-70 wt % hydroxypropyl methylcellulose (Methocel E4M Premium CR), water as volatile solvent.

The invention provides a transdermal pharmaceutical composition in a liquid formulation comprising: a first active agent selected from the group consisting of Doxylamine free base, a pharmaceutically acceptable salt of Doxylamine, and combinations thereof; a second active agent selected from the group consisting of Pyridoxine free base, a pharmaceutically acceptable salt of Pyridoxine, active metabolites thereof, and combinations thereof; and a vehicle system wherein the vehicle system comprises excipients selected from the group consisting of solvents, enhancers, pH adjusting agents, and combinations thereof. The invention provides a pharmaceutical composition of the invention wherein: Doxylamine is present in an amount selected from the group consisting of between 0.5-49 wt %, between 2-30 wt %, between 5-20 wt %; Pyridoxine is present in an amount selected from the group consisting of between 0.5-49 wt %, between 2-30 wt %, between 5-20 wt %, and wherein the vehicle system is present in an amount selected from the group consisting of between 2-99 wt %, preferably between 40-96 wt %, and between 60-90 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a liquid formulation comprising: at least one active agent selected from the group consisting of Doxylamine free base, a pharmaceutically acceptable salt of Doxylamine, and combinations thereof; and a vehicle system wherein the vehicle system comprises excipients selected from the group consisting of solvents, enhancers, pH adjusting agents, and combinations thereof. The invention provides a pharmaceutical composition wherein: Doxylamine is present in an amount selected from the group consisting of between 0.5-80 wt %, between 2-30 wt %, between 5-20 wt %, and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a liquid formulation comprising: at least one active agent selected from the group consisting of Pyridoxine free base, a pharmaceutically acceptable salt of Pyridoxine, active metabolites thereof, and combinations thereof; and a vehicle system wherein the vehicle system comprises excipients selected from the group consisting of solvents, enhancers, pH adjusting agents, and combinations thereof. The invention provides a pharmaceutical composition wherein: Pyridoxine is present in an amount selected from the group consisting of between 0.5-80 wt %, between 2-30 wt %, and between 5-20 wt %, wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a semisolid formulation comprising: a first active agent selected from the group consisting of Doxylamine free base, a pharmaceutically acceptable salt of Doxylamine, and combinations thereof; a second active agent selected from the group consisting of Pyridoxine free base, a pharmaceutically acceptable salt of Pyridoxine, active metabolites thereof, and combinations thereof; and a vehicle system wherein the vehicle system comprises excipients selected from the group consisting of solvents, enhancers, polymers, gelling agents, thickening agents, pH adjusting agents, and combinations thereof. The invention provides a pharmaceutical composition wherein: Doxylamine is present in an amount selected from the group consisting of between 0.5-49 wt %, between 2-30 wt %, and between 5-20 wt %; Pyridoxine is present in an amount selected from the group consisting of between 0.5-49 wt %, between 2-30 wt %, and between 5-20 wt %; and wherein the vehicle system is present in an amount selected from the group consisting of between 2-99 wt %, between 40-96 wt %, and between 60-90 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition as a semisolid formulation comprising: at least one active agent selected from the group consisting of Doxylamine free base, a pharmaceutically acceptable salt of Doxylamine, and combinations thereof; and a vehicle system wherein the vehicle system comprises excipients selected from the group consisting of solvents, enhancers, polymers, gelling agents, thickening agents, pH adjusting agents, and combinations thereof. The invention provides a pharmaceutical composition wherein: Doxylamine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a semisolid formulation comprising: at least one active agent selected from the group consisting of Pyridoxine free base, a pharmaceutically acceptable salt of Pyridoxine, active metabolites thereof, and combinations thereof; and a vehicle system wherein the vehicle system comprises excipients selected from the group consisting of solvents, enhancers, polymers, gelling agents, thickening agents, pH adjusting agents, and combinations thereof. The invention provides a pharmaceutical composition wherein:

Pyridoxine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a polymer matrix comprising: a first active agent selected from the group consisting of Doxylamine free base, a pharmaceutically acceptable salt of Doxylamine, and combinations thereof; a second active agent selected from the group consisting of Pyridoxine free base, a pharmaceutically acceptable salt of Pyridoxine, active metabolites thereof, and combinations thereof; and a vehicle system wherein the vehicle system comprises excipients selected from the group consisting of solvents, enhancers, plasticizers, polymers, pH adjusting agents, and combinations thereof. The invention provides a pharmaceutical composition wherein: Doxylamine is present in an amount selected from the group consisting of between 0.5-49 wt %, between 2-30 wt %, and between 5-20 wt %; Pyridoxine is present in an amount selected from the group consisting of between 0.5-49 wt %, between 2-30 wt %, and between 5-20 wt %; and wherein the vehicle system is present in an amount selected from the group consisting of between 2-99 wt %, between 40-96 wt %, and between 60-90 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a polymer matrix comprising: at least one active agent selected from the group consisting of Doxylamine free base, a pharmaceutically acceptable salt of Doxylamine, and combinations thereof; and a vehicle system wherein the vehicle system comprises excipients selected from the group consisting of solvents, enhancers, plasticizers, polymers, pH adjusting agents, and combinations thereof. The invention provides a pharmaceutical composition wherein: Doxylamine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a transdermal pharmaceutical composition in a polymer matrix comprising: at least one active agent selected from the group consisting of Pyridoxine free base, a pharmaceutically acceptable salt of pyridoxine, active metabolites thereof, and combinations thereof; and a vehicle system wherein the vehicle system comprises excipients selected from the group consisting of solvents, enhancers, plasticizers, polymers, pH adjusting agents, and combinations thereof. The invention provides a pharmaceutical composition wherein: Pyridoxine is present in an amount selected from the group consisting of between 0.5-80 wt %, between 2-30 wt %, and between 5-20 wt %; and wherein the vehicle system is present in an amount selected from the group consisting of between 20-99.5 wt %, between 70-98 wt %, and between 80-95 wt %.

The invention provides a method of treating and/or preventing nausea or nausea and vomiting in a patient comprising: selecting a patient in need of treating and/or preventing nausea or nausea and vomiting; administering to the patient the transdermal pharmaceutical composition of the invention, wherein nausea or nausea and vomiting is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a method of treating and/or preventing nausea and vomiting in pregnancy (NVP) in a patient comprising: selecting a patient in need of treating and/or preventing NVP; administering to the patient the transdermal pharmaceutical composition of the invention, wherein NVP is treated and/or prevented in the patient. The invention provides a method wherein the application is topical and wherein frequency of topical application is selected from the group consisting of once in a day, once in two days, once in three days, once in four days, once in five days, once in six days, once in a week, once in ten days, and once in fifteen days.

The invention provides a compositing comprising doxylamine and/or pyridoxine for use in the preparation of a medicament for use in treating and/or preventing nausea and vomiting. The invention provides a compositing comprising doxylamine and/or pyridoxine for use in the preparation of a medicament for use in treating and/or preventing NVP.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
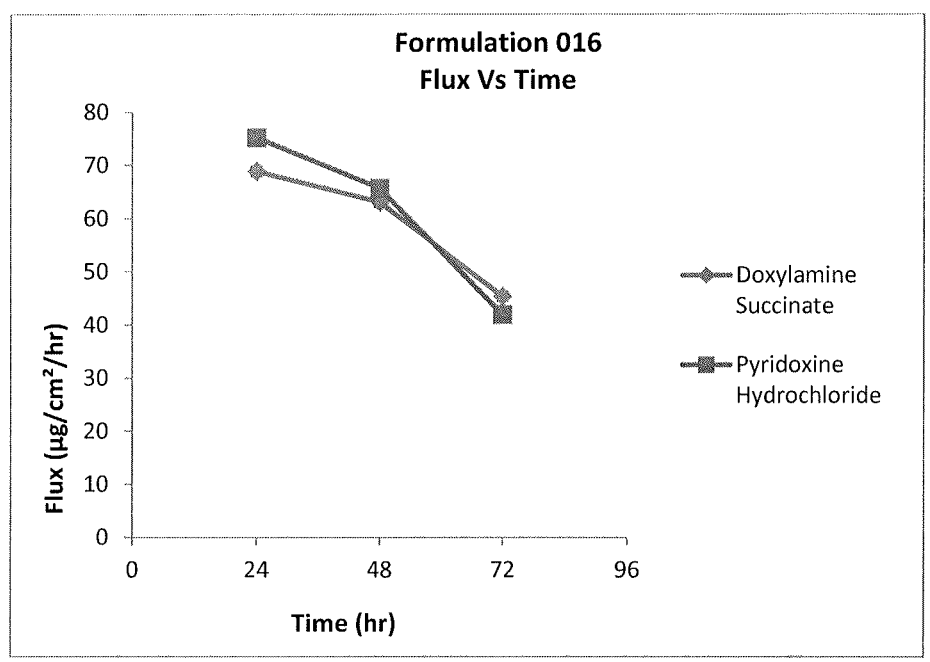
FIG. 1 is a graph of liquid Formulation 016 Flux ($\mu g/cm^2/hr$) Vs Time (hr), showing simultaneous in vitro release of Doxylamine Succinate and Pyridoxine Hydrochloride for a period of three days (72 hr) through human cadaver skin.

Doxylamine refers to all pharmaceutically acceptable forms of doxylamine either alone or in combinations thereof, for example in following forms but not limited to such as free base or salt or isomer or amorphous or crystalline or co crystalline or solid solution or prodrug or analog or derivatives or metabolites.

Pyridoxine refers to all pharmaceutically acceptable forms of pyridoxine either alone or in combinations thereof, for example in following forms but not limited to such as free base or salt or vitamin b6 analog or isomer or amorphous or crystalline or co crystalline or solid solution or prodrug or derivatives or metabolites or metabolites either alone or in combinations thereof for example in following forms but not limited to such as base, salt or analog or isomer or amorphous or crystalline or co crystalline or solid solution or prodrug or derivatives.

NVP: Nausea and vomiting in Pregnancy

The terms transdermal and topical are used interchangeably.

The terms pharmaceutical composition and formulation are used interchangeable.

The terms transdermal composition and Pharmaceutical composition are used interchangeably.

The term DICLEGIS and DICLECTIN® are used interchangeably.

Terms reservoir system and reservoir patch are used interchangeably.

Terms matrix system and matrix patch are used interchangeably.

The Term liquid includes without any limitation solution, suspension, micro suspension, nano suspension, dispersion, sprays, aerosols, emulsions, where solutions and suspension are preferred.

The term semisolid includes without any limitation such as gels, ointments, creams, emulsion, microemulsion, nanoemulsion, suspension, paste, balms, magma, lotions, mousses, waxes, liposomes, where gels are preferred.

The term polymer matrix includes polymer without any limitation pressure sensitive adhesive and/or non-adhesive polymer.

The term active substance refers to Doxylamine Succinate and/or Pyridoxine Hydrochloride.

Without limiting in scope, enhancers, solvents, polymers, gelling agents, thickening agents, suspending agents used in liquid formulations, semisolid formulations and polymer matrix can be used in other liquid formulation, polymer matrix and semisolid formulations.

The terms Transdermal delivery system refers to Transdermal patch, patch, reservoir patch, matrix patch, extended release transdermal films, plasters, multi laminate drug in adhesive patch, monolithic drug in adhesive patch, tapes, band-aid, micro-reservoir system, matrix dispersion system, adhesive dispersion system, membrane modulated system and systems which can be topically applied to skin, patches known to those skilled in the art, and microneedle systems, comprising a pharmaceutical composition according to the invention.

Topical administration includes administration to the skin or mucosa Administration of the compositions according to the present invention may be via any common topical route so long as the target tissue is available via that route. This includes direct topical administration to an affect area of, for example, the skin or mucosal surface or scalp or genital area.

All the pharmaceutical compositions or formulations are weight by weight percent.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "agent" refers to any molecule, compound, methodology and/or substance for use in the prevention, treatment, management and/or diagnosis of a disease or condition. As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for the purpose of treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, such as cancer, and/or the amelioration of one or more symptoms thereof resulting from the administration of one or more therapies.

The term "derivative" or "derivatized" as used herein includes chemical modification of a compound of the invention, or pharmaceutically acceptable salts thereof or mixtures thereof. That is, a "derivative" may be a functional equivalent of a compound of the invention, which is capable of inducing the improved pharmacological functional activity in a given subject. Illustrative of such chemical modifications would be replacement of hydrogen by a halo group, an alkyl group, an acyl group or an amino group.

As used herein, the term "pharmaceutically acceptable salts" includes acid addition salts or addition salts of free bases. The term "pharmaceutically acceptable salts" of a compound of the invention is also meant to include within its scope all the possible isomers and their mixtures, and any pharmaceutically acceptable metabolite, bioprecursor and/or pro-drug, such as, for example, a compound which has a structural formula different from the one of the compounds of the invention, and yet is directly or indirectly converted in vivo into a compound of the invention, upon administration to a subject, such as a mammal, particularly a human being.

The compound may be in the form of a pharmaceutically acceptable salt, such as an acid addition salt or a base salt, or a solvate thereof, including a hydrate thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases drug upon application to the skin (or any other surface noted above). A transdermal drug delivery system may comprise a drug-containing composition, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. Typically, transdermal drug delivery systems are classified into one of two categories: matrix-type systems and reservoir-type systems, as discussed in more detail below.

A transdermal drug delivery system also may include a drug impermeable backing layer or film. In some embodiments, the backing layer is adjacent the drug-containing composition. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's SCOTCH PAK® 1012 or 9732 (a polyester film with an ethylene vinyl acetate copolymer heat seal layer), 9723 (a laminate of polyethylene and polyester), or CoTran 9720 (a polyethylene film) are useful in the transdermal drug delivery systems described herein, as are DOW® backing layer films, such as DOW® BLF 2050 (a multi-layer backing comprising ethylene vinyl acetate layers and an internal SARAN® layer.

A transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated BIO-RELEASE® liner and SYL-OFF® 7610, Loparex's PET release liner (silicone-coated) and 3M's 1020, 1022, 9741, 9744, 9748, 9749 and 9755 SCOTCHPAK™ (fluoropolymer-coated polyester films).

A transdermal drug delivery system may be packaged or provided in a package, such as a pouchstock material used in the prior art for transdermal drug delivery systems in general. For example, DuPont's SURLYN® can be used in a pouchstock material. Alternatively, a pouchstock comprising a coextruded ethylene acrylic acid/low-density polyethylene (EAA/LDPE) material, or BAREX® from INEOS (acrylonitrile-methyl acrylate) may be used.

Doxylamine Succinate[6]
Chemical Name: ethanamine, N,N-dimethyl-2-[1-phenyl-1-(2-pyridinyl)ethoxy]-butanedioate(1:1)
Empirical Formula: $C_{17}H_{22}N_2O.C_4H_6O_4$
Molecular mass: 388.46
Classification: Antihistamine
The doxylamine succinate Structural Formula is shown below as Formula I

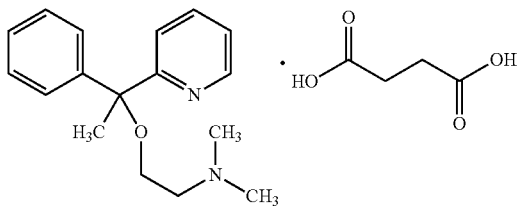

Formula I

Pyridoxine Hydrochloride[6]
Chemical Name: 3, 4-pyridinedimethanol,5-hydroxy-6-methyl-,hydrochloride
Empirical Formula: $C_8H_{11}NO_3.HCl$
Molecular mass: 205.64
Classification: Vitamin B6 analog
The pyridoxine hydrochloride Structural Formula is shown below as Formula II

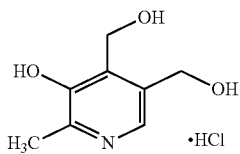

Formula II

Enhancers suitable for use include surfactants, pyrrolidone, amide, sulfoxide, fatty acids, alcohol, fatty alcohol and glycol, ethers, urea, polyoxyethylene fatty, ether alcohol, diethanolamine, essential oils, terpene, esters, polyoxyethylene fatty acid esters, esters of fatty alcohols, esters of long chain fatty acids with methyl, ethyl or isopropyl alcohol, esters of fatty alcohols with acetic acid, lactic acid, as well as oleic acid, dicarboxylic acid esters, nanocarriers, transcarbam, capsaicin derivatives, peptides, iminosulfuranes, triglycerides, hydrocarbons, phospholipids either alone or in combinations thereof.

Polymers suitable for use include cellulose and its derivatives, synthetic polymers and its derivatives such as without any limitation to carboxyvinyl polymers or carbomers, clays, all water swellable polymers, organic solvent swellable polymers, natural polymers, polysaccharides and its derivatives, resins, silicon dioxide, polyethylene and its co-polymers etc, polyvinyl alcohol, polyacrylamide, polyacrylamide, polyvinylpyrrolidone homopolymer and polyvinyl pyrrolidone copolymers, acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, pressure sensitive adhesives based on silicone, acrylic copolymer adhesives, hot melt adhesive either alone or in combinations thereof.

Plasticizers suitable for use include glycerol and its esters, phosphate esters, glycol derivatives, sugar alcohols, sebacic acid esters, azelate, citric acid esters, tartaric acid esters, adipate, phthalic acid esters, triacetin, oleic acid esters, glycerine either alone or in combinations thereof.

In one aspect invention further provides an exemplary polymer matrix of the invention further comprising about 0.5-45 wt % Doxylamine Succinate, 0.5-45 wt % Pyridoxine Hydrochloride, 1-50 wt % dimethylsulfoxide, 0.5-50 wt % glycerine, 0.5-50 wt % diethylene glycol monoethyl ether, 0.5-50 wt % propylene glycol monolaurate type (II), 0.5-70 wt % bentonite, 0.5-70 wt % hydroxypropyl methylcellulose (Methocel E4M Premium CR), water as volatile solvent.

Furthermore the invention provides exemplary pharmaceutical formulations with continuous, simultaneous in vitro transdermal delivery of Doxylamine Succinate and Pyridoxine Hydrochloride for periods of 1-3 days and 1-7 days.

In one aspect the Pharmaceutical compositions for transdermal delivery of Doxylamine Succinate and Pyridoxine Hydrochloride in pregnant women comprises Doxylamine Succinate, Pyridoxine Hydrochloride and a Vehicle system wherein pharmaceutical compositions are liquid formulations, semisolid formulations and a polymer matrix. The pharmaceutical composition can be applied topically to intact skin. Furthermore, the pharmaceutical composition can be incorporated into a transdermal delivery system which can be applied topically to intact skin. Depending the severity of symptoms, the duration of application of a transdermal delivery system or pharmaceutical composition to intact skin can be once in a day, once in two days, once in three days, once in four days, once in five days, once in six days, once in a week, or once in 10 days.

In another aspect for transdermal delivery of Doxylamine comprise a Vehicle system wherein pharmaceutical compositions are liquid formulations or semisolid formulations. The pharmaceutical composition can be applied topically. Furthermore, the pharmaceutical composition can be incorporated in transdermal delivery system.

In yet another aspect for transdermal delivery of Pyridoxine comprise a Vehicle system wherein pharmaceutical compositions are liquid formulations and semisolid formulations. The pharmaceutical composition can be applied topically. Furthermore, the pharmaceutical composition can be incorporated in transdermal delivery system.

The invention provides Novel pharmaceutical compositions for transdermal delivery of Doxylamine and/or Pyridoxine as liquid formulations, semisolid formulations and a polymer matrix. Novel Pharmaceutical compositions with Doxylamine Succinate and Pyridoxine Hydrochloride are preferred.

In one embodiment, the invention provides pharmaceutical compositions as Liquid formulations for transdermal delivery of Doxylamine and/or Pyridoxine. In one aspect the invention further provides liquid formulations comprising Doxylamine, Pyridoxine and a Vehicle system. In another aspect the invention further provides liquid formulations comprising Doxylamine and a Vehicle system. In yet another aspect the invention further provides liquid formulation comprising Pyridoxine and a Vehicle system. The invention further provides the vehicle system which comprises solvents, enhancers, and, if required, pH adjusting agents either alone or in combinations thereof. The liquid formulation comprising Doxylamine Succinate, Pyridoxine Hydrochloride and vehicle system is preferred. Without limiting in scope the liquid formulation can be a solution, suspension, emulsion, micro suspension, nano suspension, dispersion, sprays, aerosols, where solutions, suspension are preferred. Without limiting in scope Doxylamine Succinate and/or Pyridoxine Hydrochloride in the liquid formulation can be dissolved and/or suspended.

In one aspect the liquid formulation is comprised of Doxylamine Succinate, Pyridoxine Hydrochloride and a Vehicle system wherein, Doxylamine Succinate is present in an amount between 0.5-49 wt %, Pyridoxine Hydrochloride is present in an amount between 0.5-49 wt %, vehicle system is present in an amount between 2-99 wt %. More preferably, Doxylamine Succinate is present in an amount between 5-30 wt %, Pyridoxine Hydrochloride is present in an amount between 5-30 wt %, vehicle system is present in an amount between 40-90 wt %. The invention further provides an exemplary liquid composition of the invention comprising about 0.5-40 wt % Doxylamine Succinate, 0.5-40 wt % Pyridoxine Hydrochloride, 0.5-96 wt % dimethylsulfoxide, 0.5-96 wt % ethanol, 0.5-96 wt % dipropylene glycol, 0.5-96 wt % diethylene glycol monoethyl ether, 0.5-96 wt % propylene glycol monolaurate type (II), 0.5-96 wt % water, pH between 3-8. More Preferably, about 5-30 wt % Doxylamine Succinate, 5-30 wt % Pyridoxine Hydrochloride, 5-45 wt % dimethylsulfoxide, 1-25 wt % ethanol, 1-25 wt % dipropylene glycol, 1-40 wt % diethylene glycol monoethyl ether, 1-25 wt % propylene glycol monolaurate type (II), 1-50 wt % water, pH between 4-7. Without limiting in scope an exemplary formulation 016 in this range is illustrated in Example 1.

The invention further provides another exemplary liquid composition of the invention comprising about 0.5-40 wt % Doxylamine Succinate, 0.5-40 wt % Pyridoxine Hydrochloride, 0.5-94 wt % dimethylsulfoxide, 0.5-94 wt % hexylene glycol, 0.5-94 wt % propylene glycol, 0.5-94 wt % polyethylene glycol 400, 0.5-94 wt % dipropylene glycol, 0.5-94 wt % diethylene glycol monoethyl ether, 0.5-94 wt % propylene glycol monolaurate type (II), 0.5-94 wt % water, pH between 3-8. More Preferably, about 5-30 wt % Doxylamine Succinate, 5-30 wt % Pyridoxine Hydrochloride, 5-45 wt % dimethylsulfoxide, 1-25 wt % hexylene glycol, 1-25 wt % propylene glycol, 1-25 wt % polyethylene glycol (PEG) 400, 1-25 wt % dipropylene glycol, 1-40 wt % diethylene glycol monoethyl ether, 1-25 wt % propylene glycol monolaurate type (II), 1-50 wt % water, pH between 4-7. Without limiting in scope an exemplary formulation 080 in this range is illustrated in Example 1.

In another aspect a liquid formulation is comprised Doxylamine Succinate and a Vehicle system wherein, Doxylamine Succinate is present in an amount between 0.5-80 wt %, vehicle system is present in an amount between 20-99.5 wt %. More preferably, Doxylamine Succinate is present in an amount between 5-30 wt %, vehicle system is present in an amount between 70-95 wt %. The invention further provides an exemplary liquid composition of the invention comprising about 0.5-70 wt % Doxylamine Succinate, 0.5-96 wt % dimethylsulfoxide, 0.5-96 wt % ethanol, 0.5-96 wt % dipropylene glycol, 0.5-96 wt % diethylene glycol monoethyl ether, 0.5-96 wt % propylene glycol monolaurate type (II), 0.5-96 wt % water, hydrochloric acid and/or sodium hydroxide to adjust pH between 3-8. More Preferably, about 5-40 wt % Doxylamine Succinate, 5-45 wt % dimethylsulfoxide, 1-25 wt % ethanol, 1-25 wt % dipropylene glycol, 1-40 wt % diethylene glycol monoethyl ether, 1-25 wt % propylene glycol monolaurate type (II), 1-50 wt % water, hydrochloric acid and/or sodium hydroxide to adjust pH between 4-7. Without limiting in scope an exemplary formulation 015 in this range is illustrated in Example 1.

In yet another aspect the liquid formulation is comprised of Pyridoxine Hydrochloride and Vehicle system wherein, Pyridoxine Hydrochloride is present in an amount between 0.5-80 wt %, vehicle system is present in an amount between 20-99.5 wt %. More preferably, Pyridoxine Hydrochloride is present in an amount between 5-30 wt %, vehicle system is present in an amount between 70-95 wt %. The invention further provides an exemplary liquid composition of the invention comprising about 0.5-70 wt % Pyridoxine Hydrochloride, 0.5-96 wt % dimethylsulfoxide, 0.5-96 wt % ethanol, 0.5-96 wt % dipropylene glycol, 0.5-96 wt % diethylene glycol monoethyl ether, 0.5-96 wt % propylene glycol monolaurate type (II), 0.5-96 wt % water, hydrochloric acid and/or sodium hydroxide to adjust pH between 3-8. More Preferably, about 5-40 wt % Pyridoxine Hydrochloride, 5-45 wt % dimethylsulfoxide, 1-25 wt % ethanol, 1-25 wt % dipropylene glycol, 1-40 wt % diethylene glycol monoethyl ether, 1-25 wt % propylene glycol monolaurate type (II), 1-50 wt % water, hydrochloric acid and/or sodium hydroxide to adjust pH between 4-7. Without limiting in scope an exemplary formulation 014 in this range is illustrated in Example 1.

Transdermal drug delivery provides several advantages over other routes for administering a drug formulation to a patient. One method for transdermal drug delivery involves using microneedle arrays to bypass the barrier properties of the stratum corneum. Although microneedle arrays were first reported over 15 years ago, numerous obstacles have prolonged the development of microneedle arrays and delayed its commercialization. For example, the small size of the microneedles makes verifying effective administration of the therapeutic agents difficult. Many groups have looked to use of applicators and other types of special insertion devices that are used to apply a pre-set force that will ensure that the microneedles penetrate the stratum corneum. These applicators and other insertion devices, however, can be cumbersome to use and unnecessarily increase the cost of using the microneedle arrays. In one aspect, a microneedle patch for administration of an active pharmaceutical ingredient (API) or other substance of interest into a biological tissue is provided. For example, the biological tissue may be the skin or a mucosal tissue of a human or other mammal in need of treatment or prophylaxis. The patch includes a base substrate having a microneedle side and an opposing back side with one or more solid microneedles extending from the microneedle side of the base substrate, the one or more solid microneedles including a substance of interest, such as t least one API of the invention. The patch further includes an adhesive layer and a handle layer affixed to the back side of the base substrate, the handle layer including a tab portion which extends away (e.g., laterally) from the one or more solid microneedles and permits a person to manually hold the tab portion (e.g., between a thumb and finger) to manipulate the patch without contacting the one or more solid microneedles.

In another aspect, a system for storing and transporting one or more microneedle patches is provided. The system includes one or more microneedle patches and a tray with an upper surface region surrounding one or more recessed regions. Each of the one or more recessed regions is dimensioned to receive in a non-contacting manner the one or more solid microneedles of a corresponding microneedle patch, with a portion of the adhesive layer of the microneedle patch being releasably secured to the upper surface region of the tray.

In yet another aspect, a microneedle patch for administration of at least one API of the invention or other substance of interest into a patient's skin (or into another biological tissue) including one or more feedback indicators is provided. The patch includes a base substrate having a microneedle side and an opposing back side with one or more solid microneedles extending from the microneedle side of the base substrate, wherein the one or more microneedles include the substance of interest, for example as part of the microneedle structure and/or as a coating on the microneedle structure.

In one embodiment, the microneedle patch includes a mechanical force indicator configured to provide an audible, tactile, and/or visual signal when a force applied to the patch by a user, in the course of applying the patch to a patient's skin (or into another biological tissue) to insert the one or more microneedles therein, meets or exceeds a predetermined threshold. The mechanical force indicator may be in line with and generally centered about the microneedles on the opposing back side of the base substrate.

In another embodiment, the one or more solid microneedles are dissolvable microneedles and the patch includes an indicator for providing an audible, tactile, or visual signal indicative of the one or more microneedles puncturing a patient's skin and/or completion of delivery of the substance of interest from the one or more solid microneedles in vivo following application of the patch to a patient's skin.

Methods for administering at least one API according to the invention or other substance of interest to a patient with a microneedle patch are also provided. The methods include removing the microneedle patch from a tray in which the microneedle patch is releasably secured by manually grasping a tab portion of the microneedle patch, e.g., between the thumb and finger; applying the microneedle patch to a patient's skin; manually pressing the microneedle patch, e.g., with a finger, thumb, or heel of hand, to apply a pressure sufficient to insert the one or more microneedles into the patient's skin, and removing the microneedle patch from the patient's skin by grasping the tab portion of the microneedle patch between the thumb and finger. Similar steps could also be used to apply the patch to a biological tissue other than the skin.

The invention will be illustrated in more detail with reference to the following Examples, but it should be understood that the present invention is not deemed to be limited thereto.

EXAMPLES

Example 1

Liquid Formulations

| Ingredients | Formulation 016 (% w/w) | Formulation 080 (% w/w) |
| --- | --- | --- |
| Doxylamine Succinate | 8.95% | 9% |
| Pyridoxine Hydrochloride | 8.25% | 8.25% |
| Dimethylsulfoxide | 31% | 30.25% |
| Propylene Glycol | — | 3% |
| Dipropylene Glycol | 5.8% | 3% |
| Polyethylene Glycol 400 | — | 3% |
| Hexylene Glycol | — | 4.5% |
| Ethanol | 6% | — |
| Propylene glycol monolaurate type (II) | 4% | 4% |
| Diethylene Glycol Monoethyl Ether | 18% | 17.25% |
| Water | 18% | 17.75% |
| pH | 4.7-5.1 | 4.7-5.1 |

| Ingredients | Formulation 014 (% w/w) | Formulation 015 (% w/w) |
| --- | --- | --- |
| Doxylamine Succinate | — | 9.8% |
| Pyridoxine Hydrochloride | 9% | — |
| Dimethylsulfoxide | 34% | 34% |
| Dipropylene Glycol | 6.5% | 6.5% |
| Ethanol | 6.5% | 6.5% |
| Propylene glycol monolaurate type (II) | 4% | 4% |
| Diethylene Glycol Monoethyl Ether | 20% | 20% |
| Water qs to | 100% | 100% |
| pH adj NaOH or HCl | 5.03 | 5.10 |

In another embodiment, the invention provides pharmaceutical compositions as semisolid formulations for transdermal delivery of Doxylamine and/or Pyridoxine. In one aspect the invention further provides semisolid formulation comprising Doxylamine, Pyridoxine and a Vehicle system. In another aspect the invention further provides semisolid formulation comprising Doxylamine and a Vehicle system. In yet another aspect the invention further provides semisolid formulation comprising Pyridoxine and a Vehicle system. The invention further provides the vehicle system for semisolid formulations which comprises solvents, enhancers, polymers or gelling agents or thickening agents or suspending agents, if required pH adjusting agents either alone or in combinations thereof. The semisolid formulation comprising Doxylamine Succinate, Pyridoxine Hydrochloride and vehicle system is preferred. Without limiting in scope the semisolid formulation can be in the dosage form of gels, ointments, creams, suspension, dispersion, emulsion, microemulsion, nanoemulsion, paste, balms, magma, lotions, mousses, liposomes wherein gels are preferred. Without limiting in scope Doxylamine Succinate and/or Pyridoxine Hydrochloride in the semisolid formulation can be dissolved and/or suspended.

In one aspect the semisolid formulation is comprised of Doxylamine Succinate, Pyridoxine Hydrochloride and Vehicle system wherein, Doxylamine Succinate is present in an amount between 0.5-49 wt %, Pyridoxine Hydrochloride is present in an amount between 0.5-49 wt %, vehicle system is present in an amount between 2-99 wt %. More preferably, Doxylamine Succinate is present in an amount between 5-30 wt %, Pyridoxine Hydrochloride is present in an amount between 5-30 wt %, vehicle system is present in an amount between 40-90 wt %.

The invention further provides an exemplary semisolid formulation comprising about 0.5-40 wt % Doxylamine Succinate, 0.5-40 wt % Pyridoxine Hydrochloride, 0.5-95 wt % dimethylsulfoxide, 0.5-95 wt % hexylene glycol, 0.5-95 wt % diethylene glycol monoethyl ether, 0.5-95 wt % propylene glycol monolaurate type (II), 0.5-95 wt % water, 0.25-30 wt % hydroxypropyl cellulose HF, pH between 3-8. More Preferably, about 5-40 wt % Doxylamine Succinate, 5-40 wt % Pyridoxine Hydrochloride, 5-45 wt % dimethylsulfoxide, 1-30 wt % hexylene glycol, 1-40 wt % diethylene glycol monoethyl ether, 1-25 wt % propylene glycol monolaurate type (II), 1-50 wt % water, 1-10 wt % hydroxypropyl cellulose HF, pH between 4-7. Without limiting in scope exemplary formulation 046 in this range is illustrated in Example 2.

The invention further provides yet another exemplary semisolid formulation of the invention comprising about 0.5-40 wt % Doxylamine Succinate, 0.5-40 wt % Pyridoxine Hydrochloride, 0.5-95 wt % dimethylsulfoxide, 0.5-95 wt % hexylene glycol, 0.5-95 wt % diethylene glycol monoethyl ether, 0.5-95 wt % propylene glycol monolaurate type (II), 0.5-95 wt % glycerine, 0.5-95% wt water, 0.25-30 wt % hydroxypropyl cellulose HF, pH between 3-8. More Preferably, about 5-40 wt % Doxylamine Succinate, 5-40 wt % Pyridoxine Hydrochloride, 5-45 wt % dimethylsulfoxide, 1-30 wt % hexylene glycol, 1-40 wt % diethylene glycol monoethyl ether, 1-25 wt % propylene glycol monolaurate type (II), 1-30 wt % glycerine, 1-50 wt % water, 1-10 wt % hydroxypropyl cellulose HF, pH between 4-7. Without limiting in scope exemplary formulation 054 in this range is illustrated in Example 2.

In another aspect the semisolid formulation is comprised of Doxylamine Succinate and Vehicle system wherein, Doxylamine Succinate is present in an amount between 0.5-80 wt %, vehicle system is present in an amount between 20-99.5 wt %. More preferably, Doxylamine Succinate is present in an amount between 5-30 wt %, vehicle system is present in an amount between 70-95 wt %. The invention further provides an exemplary formulation of the invention comprising about 0.5-70 wt % Doxylamine Succinate, 0.5-95 wt % dimethylsulfoxide, 0.5-95 wt % hexylene glycol, 0.5-95 wt % diethylene glycol monoethyl ether, 0.5-95% wt propylene glycol monolaurate type (II), 0.5-95 wt % water, 0.25-30 wt % hydroxypropyl cellulose HF, hydrochloric acid and/or sodium hydroxide to adjust pH between 3-8. More Preferably, about 5-40 wt % Doxylamine Succinate, 5-45 wt % dimethylsulfoxide, 1-30 wt % hexylene glycol, 1-40 wt % diethylene glycol monoethyl ether, 1-25 wt % propylene glycol monolaurate type (II), 1-50 wt % water, 1-10 wt % hydroxypropyl cellulose HF, hydrochloric acid and/or sodium hydroxide to adjust pH between 4-7. Without limiting in scope an exemplary formulation 063 in this range is illustrated in Example 2.

In yet another aspect the semisolid formulation is comprised of Pyridoxine Hydrochloride and a Vehicle system wherein, Pyridoxine Hydrochloride is present in an amount between 0.5-80 wt %, vehicle system is present in an amount between 20-99.5 wt %. More preferably, Pyridoxine Hydrochloride is present in an amount between 5-30 wt %, vehicle system is present in an amount between 70-95 wt %. The invention further provides an exemplary semisolid formulation of the invention comprising about 0.5-70 wt % Pyridoxine Hydrochloride, 0.5-95 wt % dimethylsulfoxide, 0.5-95 wt % hexylene glycol, 0.5-95 wt % diethylene glycol monoethyl ether, 0.5-95 wt % propylene glycol monolaurate type (II), 0.5-95 wt % water, 0.25-30 wt % hydroxypropyl cellulose HF, hydrochloric acid and/or sodium hydroxide to adjust pH between 3-8. More Preferably, about 5-40 wt % Pyridoxine Hydrochloride, 5-45 wt % dimethylsulfoxide, 1-30 wt % hexylene glycol, 1-40 wt % diethylene glycol monoethyl ether, 1-25 wt % propylene glycol monolaurate type (II), 1-50 wt % water, 1-10 wt % hydroxypropyl cellulose HF, hydrochloric acid and/or sodium hydroxide to adjust pH between 4-7. Without limiting in scope an exemplary formulation 064 in this range is illustrated in Example 2.

Example 2

Semisolid Formulations

| Ingredient | Formulation 046 (% w/w) | Formulation 054 (% w/w) |
|---|---|---|
| Doxylamine Succinate | 9% | 9% |
| Pyridoxine Hydrochloride | 8.25% | 8.25% |
| Dimethylsulfoxide | 30.25% | 32.25% |
| Propylene glycol monolaurate type (II) | 4% | 4% |
| Diethylene Glycol Monoethyl Ether | 17.25% | 17.25% |
| Hexylene Glycol | 10% | 10% |
| Glycerine | — | 3% |
| Water | 17.75% | 12.75% |
| Hydroxypropyl cellulose HF | 3.50% | 3.50% |
| pH | 4.8-5.1 | 4.8-5.1 |

| Ingredient | Formulation 063 (% w/w) | Formulation 064 (% w/w) |
|---|---|---|
| Doxylamine Succinate | 9% | — |
| Pyridoxine Hydrochloride | — | 8.25% |
| Dimethylsulfoxide | 30.25% | 30.25% |
| Propylene glycol monolaurate type (II) | 4% | 4% |
| Diethylene Glycol Monoethyl Ether | 17.25% | 17.25% |
| Hexylene Glycol | 18.25% | 19% |
| Hydroxypropyl cellulose HF | 3.50% | 3.50% |
| Water qs | 100% | 100% |
| pH adj with NaOH/HCl | 5.00 | 5.00 |

In yet another embodiment, the invention provides pharmaceutical compositions as a polymer matrix for transdermal delivery of Doxylamine and/or Pyridoxine. In one aspect the invention further provides a polymer matrix comprised of Doxylamine, Pyridoxine and a Vehicle system. In another aspect the invention further provides a polymer matrix comprised of Doxylamine and a Vehicle system. In yet another aspect the invention further provides a polymer matrix comprised of Pyridoxine and a Vehicle system. The invention further provides a vehicle system for polymer matrix, comprising: solvents, plasticizers, enhancers, polymers, and, if required, pH adjusting agents either alone or on combinations thereof. In addition vehicle system for polymer matrix if required may also comprise tackifiers, fillers.

In one aspect the Polymer matrix is comprised of Doxylamine Succinate, Pyridoxine Hydrochloride and Vehicle system wherein, Doxylamine Succinate is present in an amount between 0.5-49 wt %, Pyridoxine Hydrochloride is present in an amount between 0.5-49 wt %, vehicle system is present in an amount between 2-99 wt %. More preferably, Doxylamine Succinate is present in an amount between 5-30 wt %, Pyridoxine Hydrochloride is present in an amount between 5-30 wt %, vehicle system is present in an amount between 40-90 wt %. The invention further provides an exemplary polymer matrix of the invention comprising about about 0.5-45 wt % Doxylamine Succinate, 0.5-45 wt % Pyridoxine Hydrochloride, 1-50 wt % dimethylsulfoxide, 0.5-50 wt % glycerine, 0.5-50 wt % diethylene glycol monoethyl ether, 0.5-50 wt % propylene glycol monolaurate type (II), 0.5-70 wt % bentonite, 0.5-70 wt % hydroxypropyl methylcellulose (Methocel E4M Premium CR). To prepare the polymer matrix water was used as a volatile solvent. Without limiting in scope an exemplary formulation M001 in this range is illustrated in Example 3

The invention further provides another exemplary polymer matrix of the invention comprising about 0.5-45 wt % Doxylamine Succinate, 0.5-45 wt % Pyridoxine Hydrochloride, 0.5-50 wt % dimethylsulfoxide, 0.5-30 wt % propylene glycol monolaurate type (II), 0.5-30 wt % oleic acid, 0.5-70 wt % DURO-TAK® 387-2516 (wherein DURO-TAK 387-2516 is an acrylic adhesive).

In another aspect the Polymer matrix is comprised of Doxylamine Succinate and a Vehicle system wherein, Doxylamine Succinate is present in an amount between 0.5-50 wt % and vehicle system is present in an amount between 50-99.5 wt %. More preferably, Doxylamine Succinate is present in an amount between 5-30 wt %, vehicle system is present in an amount between 70-95 wt %.

In another aspect the Polymer matrix is comprised of Pyridoxine Hydrochloride and a Vehicle system wherein, Pyridoxine Hydrochloride is present in an amount between 0.5-50 wt % and vehicle system is present in an amount between 50-99.5 wt %. More preferably, Pyridoxine Hydrochloride is present in an amount between 5-30 wt %, vehicle system is present in an amount between 70-95 wt %.

Example 3

Polymer Matrix

| Ingredient | Formulation M001 (% w/w) |
| --- | --- |
| Doxylamine Succinate | 8.5% |
| Pyridoxine Hydrochloride | 8.5% |
| Dimethylsulfoxide | 13.5% |
| Diethylene glycol monoethyl ether | 10.5% |
| Propylene Glycol Monolaurate (type II) | 4% |
| Glycerine | 26% |
| Bentonite | 15% |
| Hydroxypropyl methylcellulose (Methocel E4M Premium CR) | 14% |

Optimum mixture experiments were used to select the level of the variables in pharmaceutical compositions comprising liquid formulations, semisolid formulations and polymer matrix.

The effect of different amount of Doxylamine Succinate and Pyridoxine Hydrochloride on the in vitro flux or release profile of doxylamine succinate and pyridoxine hydrochloride were evaluated using human cadaver skin.

The concentration or amount of drug in the pharmaceutical composition influences the drug delivery or flux. The invention further provides, different amount of Doxylamine Succinate and Pyridoxine Hydrochloride in pharmaceutical compositions. The amount of Doxylamine Succinate and Pyridoxine Hydrochloride in liquid formulations, semisolid formulations and polymer matrix is about 0.5%-49 wt % Doxylamine Succinate and 0.5-49% Pyridoxine Hydrochloride. Preferably about 1-30 wt % Doxylamine Succinate and about 1-30 wt % Pyridoxine Hydrochloride, more preferably for liquid formulations and semisolid formulations about 2-25 wt % for Doxylamine Succinate and 2-25 wt % for Pyridoxine Hydrochloride, more preferably for polymer matrix about 0.5%-30 wt % Doxylamine Succinate and 0.5-30 wt % Pyridoxine Hydrochloride. Without limiting in scope few exemplary formulations in this range are illustrated in example 4.

Example 4

Formulations with Different Amounts of Doxylamine Succinate and Pyridoxine Hydrochloride

| Ingredients | Formulation 051 (% w/w) | Formulation 052 (% w/w) | Formulation 053 (% w/w) |
| --- | --- | --- | --- |
| Doxylamine Succinate | 6.75% | 4.5% | 2.25% |
| Pyridoxine Hydrochloride | 6.75% | 4.5% | 2.25% |
| Dimethylsulfoxide | 30.25% | 30.25% | 30.25% |
| Propylene glycol monolaurate type (II) | 4% | 4% | 4% |
| Diethylene Glycol Monoethyl Ether | 17.25% | 17.25% | 17.25% |
| Hexylene Glycol | 10% | 10% | 10% |
| Propylene glycol | 3.75% | 8.25% | 13.75% |
| Water | 17.75% | 17.75% | 16.75% |
| Hydroxypropyl cellulose HF | 3.50% | 3.50% | 3.50% |

An optimum mixture design of experiments was used to select the level of the vehicle system variables. The effect of solvents, enhancers and gelling agents or thickening agent or polymers on the in vitro flux or release profile of doxylamine succinate and pyridoxine hydrochloride were evaluated using human cadaver skin.

Optimum mixture experiments were used to select the level of the vehicle system variables which includes solvents, enhancers and gelling agents or thickening agent or polymers.

Solvents suitable for use in the present invention include but are not limited to alcohol (such as but not limited to ethanol, isopropyl alcohol, butanol, $C_1$-$C_{20}$ alcohol etc), sulfoxide (such as but not limited to dimethylsulfoxide, decylmethylsulfoxide, etc), polyhydric alcohols (such as but not limited to mannitol, sorbitol, xylitol, glycerol etc), glycol ethers (such as but not limited to diethylene glycol monoethyl ether etc), vegetable oil, acids (such as but not limited to lactic acid, levulinic acid, adipic acid, alginic acid, ascorbic acid, etc), polar solvents (such as but limited to water, etc), non-polar solvents, semi polar solvents, volatile solvents (such as but not limited to ethanol, propanol, ethyl acetate, methanol, dichloromethane, isopropyl alcohol, chloroform, toluene, acetone, etc) and, water, pyrrolidone (such as but not limited to N-methyl 2-pyrrolidone, 2-pyrrolidone, etc), dimethyl isosorbide, emulsifying agents (such as but not limited to anionic, cationic, sulfates, nonionic, sulfonates, natural, finely divided solids, sorbitan trioleate, sucrose distearate, sodium oleate etc), surfactants such as but not limited to tween, polysorbate (such as but not limited to tween 20, tween 40, tween 60, tween 80 etc), span (such as but not limited to span 20, span 80 etc), propylene glycol dicaprylate, medium chain triglycerides, linoleoyl polyoxyl-6 glycerides, Caprylic glyceride, oleoyl-polyoxyl-6-glycerides, lauroyl polyoxyl-6-gylcerides, polyglyceryl-3-dioleate, cyclodextrins etc, Glycol (such as but not limited to hexylene glycol, dipropylene glycol, polyethylene glycol, butylene glycol, propylene glycol, tripropylene glycol, polypropylene glycol etc), derivatives of glycols, skin irritation reducing agents, emollients, humectants and similar compounds (such as but not limited to glycerol, petrolatum, mineral oil, lanolin, dimethicone, vegetable oil, zinc oxide, vitamin E, lecithin, propylene glycol etc), tetrahydrofurfuryl alcohol, diethyl tolumide, monoisopropylidene glycerine, either alone or in combinations thereof. Preferred solvents are sulfoxide, alcohol, glycols, acid, glycol ethers, polar solvents, and pyrrolidone. More preferably, dimethylsulfoxide, propylene glycol, dipropylene glycol, hexylene glycol, polyethylene glycol, lactic acid, N-Methyl pyrrolidone, diethylene glycol monoethyl ether, glycerine and water. Without limiting in scope a few exemplary formulations with solvents are illustrated in example 5.

Example 5

Formulations with Different Solvents

| Ingredients | Formulation 029 (% w/w) | Formulation 063 (% w/w) | Formulation 068 (% w/w) |
|---|---|---|---|
| Doxylamine Succinate | 7% | 9% | 9% |
| Pyridoxine Hydrochloride | 7% | 8.25% | 8.25% |
| Dimethylsulfoxide | 10% | 30.25% | 30.25% |
| Propylene Glycol | 18.25% | — | — |
| Dipropylene Glycol | 5% | — | — |
| Polyethylene glycol 400 | — | — | — |
| Hexylene Glycol | — | 27.25% | 10% |
| Lactic acid | 5% | — | — |
| N-Methyl Pyrrolidone | — | — | 4% |
| Propylene glycol monolaurate type (II) | 4% | 4% | — |
| Diethylene Glycol Monoethyl Ether | 24% | — | 17.25% |
| Water | 17.75% | 17.75% | 17.75% |
| Hydroxypropyl Cellulose HF | 2% | 3.5% | 3.5% |

Enhancers are used for penetration or permeation enhancement of active substance through the skin. Enhancers suitable for use in the present invention include but are not limited to surfactants (such as but not limited to anionic, cationic, nonionic, amphoteric surfactants, polysorbate, span, tween, sodium lauryl sulfate, propylene glycol monolaurate type (II), propylene glycol monolaurate type (I), propylene glycol monocaprylate type (II), propylene glycol monocaprylate type (I), propylene glycol dicaprylate etc), fatty acids (such as but not limited to oleic acid, capric acid, caprylic acid, lauric acid, myristic acid, linoleic acid, stearic acid, palmitic acid, etc), alcohol, fatty alcohols and glycol (such as but not limited to ethanol, oleyl alcohol, dodecanol, propylene glycol, glycerol, propylene glycol, etc), esters, fatty acid esters and fatty alcohol esters (such as but not limited to ethyl oleate, butyl ethanoate, ethyl ethanoate, methyl ethanoate, oleyl oleate, isopropyl myristate, isopropyl palmitate, decyl oleate, lauryl lactate, lauryl laurate, glycerol monooleate, glycerol monolaurate etc), esters of long chain fatty acids with methyl, ethyl, isopropyl alcohols, esters of fatty alcohols with acetic acid, lactic acid as well as oleic acid, diethanolamine, essential oils, terpene and terpenoids (such as but not limited to terpineol, limonene, thymol, cineole etc), amides (such as but not limited to azone, dimethylacetamide, dimethylformamide etc), urea, polyoxyethylene fatty alcohol ethers, polyoxyethylene fatty acid esters, sulfoxide (such as but not limited to dimethyl sulfoxide, decyl methyl sulfoxide, etc), triglycerides (such as but not limited to triacetin etc), ether alcohol (such as but not limited to diethylene glycol monoethyl ether, ethylene glycol monoethyl ether etc), pyrrolidones (such as but not limited to N-methyl-2-pyrrolidone, 2-pyrrolidone etc), hydrocarbons (such as but not limited to alkanes, squalene etc), phospholipids (such as but not limited to lecithin, etc.), transcarbam, capsaicin derivatives, dimethylamino acid esters, peptides, iminosulfuranes, dicarboxylic acid esters, nanocarriers (such as but not limited to surfactant based vesicles, lipid based vesicles, lipid based particulate carriers etc) either alone or in combinations thereof, all penetration or permeation enhancers referred in the book "Percutaneous Penetration Enhancers" (Eric W. Smith, Howard I. Maibach, 2005. November, CRC press). Preferred enhancers are surfactants, fatty acid, fatty acid esters, fatty alcohol, terpene, urea, triglycerides. More preferably, propylene glycol monolaurate type (II), propylene glycol monolaurate type (I), propylene glycol monocaprylate type (II), tween 20, span 20, lauryl lacate, oleic acid, terpineol, urea, oleyl alcohol, triacetin. Without limiting in scope a few exemplary formulations with enhancers are illustrated in example 6.

Example 6

Formulations with Different Enhancers

| Ingredients | Formulation 027 (% w/w) | Formulation 058 (% w/w) | Formulation 060 (% w/w) | Formulation 061 (% w/w) | Formulation 062 (% w/w) |
|---|---|---|---|---|---|
| Doxylamine Succinate | 9.5% | 9% | 9% | 9% | 9% |
| Pyridoxine Hydrochloride | 8.85% | 8.25% | 8.25% | 8.25% | 8.25% |
| Dimethylsulfoxide | 28% | 30.25% | 30.25% | 30.25% | 30.25% |
| Hexylene Glycol | — | 10% | 10% | 10% | 10% |
| Dipropylene Glycol | 5% | — | — | — | — |
| Tween 20 | 3.7% | — | — | — | — |
| Lauryl Lactate | — | — | 4% | — | — |
| Oleic acid | — | — | — | 4% | — |
| Propylene Glycol Monocaprylate Type (II) | — | 4% | — | — | — |
| Terpineol | — | — | — | — | 4% |
| Propylene glycol monolaurate type (II) | 3.7% | — | — | — | — |
| Diethylene Glycol Monoethyl Ether | 22% | 17.25% | 17.25% | 17.25% | 17.25% |

-continued

| Ingredients | Formulation 027 (% w/w) | Formulation 058 (% w/w) | Formulation 060 (% w/w) | Formulation 061 (% w/w) | Formulation 062 (% w/w) |
| --- | --- | --- | --- | --- | --- |
| Water | 17.25% | 17.75% | 17.75% | 17.75% | 17.75% |
| Hydroxypropyl Cellulose HF | 2% | 3.5% | 3.5% | 3.5% | 3.5% |

Formulations with Different Enhancers

| Ingredients | Formulation 060 (% w/w) | Formulation 075 (% w/w) | Formulation 076 (% w/w) | Formulation 077 (% w/w) |
| --- | --- | --- | --- | --- |
| Doxylamine Succinate | 9% | 9% | 9% | 9% |
| Pyridoxine Hydrochloride | 8.25% | 8.25% | 8.25% | 8.25% |
| Dimethylsulfoxide | 30.25% | 30.25% | 30.25% | 30.25% |
| Hexylene Glycol | 10% | 13.5% | 13.5% | 10% |
| Urea | 4% | — | — | — |
| Oleyl Alcohol | — | 0.5% | — | — |
| Span 20 | — | — | 0.5% | — |
| Triacetin | — | — | — | 4% |
| Diethylene Glycol Monoethyl Ether | 17.25% | 17.25% | 17.25% | 17.25% |
| Water | 17.75% | 17.75% | 17.75% | 17.75% |
| Hydroxypropyl Cellulose HF | 3.5% | 3.5% | 3.5% | 3.5% |

Polymers, gelling agents, thickening agents, suspending agents, and similar compounds suitable for use in semisolid formulations and a polymer matrix in the present invention include but are not limited to cellulose and its derivatives (such as but not limited to hydroxyethyl cellulose, hydroxypropyl cellulose, hydroxymethyl cellulose, carboxymethyl cellulose, hydroxypropyl methyl cellulose, hydroxypropylethyl cellulose etc), synthetic polymers and its derivatives such as without any limitation to carboxyvinyl polymers or carbomers (such as but not limited to carbopol 971pNF, carbopol 940, carbopol 934 etc), clays (such as but not limited to bentonite, kaolin, silicates etc), all water and/or organic solvent swellable polymers, natural polymers, polysaccharides and its derivatives (such as but not limited to chitosan, xanthum gum, tragacanth, potassium or sodium carrageenan, agar alginic acid and derivatives, cassia tora, collagen, gelatin, gellum gum, guar gum, pectin, gum copal, resin, starch, acacia etc), silicon dioxide, fillers (such as but not limited to polyhydric alcohol, mannitol, sorbitol, lactose etc), polyethylene and its co-polymers etc, polyvinyl alcohol, polyacrylamide, polyacrylamide, polyvinylpyrrolidone homopolymer and polyvinyl pyrrolidone copolymers (such as but not limited to PVP, poloxamer etc), eudragit, acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, pressure sensitive adhesives base on pure acrylate monomers as well as acrylate copolymers and terpolymers using for example as the monomers vinyl acetate or hydrocarbon copolymers which may include pacifiers and other pressure sensitive adhesive modifiers, pressure sensitive adhesives based on silicone, acrylic pressure sensitive adhesives (such as but not limited to DURO-TAK 87-2156, gelva gms 9073, DURO-TAK 387-2054, bio psa-4202, bio psa-4302, DURO-TAK 87-9301, DURO-TAK 87-2074, DURO-TAK 87-235A, DURO-TAK 87-2194, DURO-TAK 387-2516, DURO-TAK 387-2287 etc), hot melt adhesive, the term hot melt adhesive comprise any adhesive which are not liquefied with solvent but by melting at elevated temperature, preferably in the range of from 60-200 C, suitable as hot-melt adhesive are in particular, mixture of esters of hydrogenated colophony with cellulose derivatives either alone or in combinations thereof. Preferred polymers or gelling agents or thickening agents or suspending agents for semisolid formulations and matrix films are cellulose and its derivatives, synthetic polymers, natural polymers, clays, water swellable polymers, polyvinylpyrrolidones, pressure sensitive adhesives. More preferably, hydroxypropyl cellulose, carbopol, bentonite, polyvinyl pyrrolidone K30, chitosan, hydroxypropyl methylcellulose, eudragit, DURO-TAK pressure sensitive adhesives. Without limiting in scope a few exemplary formulations with polymers are illustrated in example 7.

Example 7

Semisolid Formulations with Different Gelling Agents or Polymers or Thickening Agents

| Ingredients | Formulation 013 (% w/w) | Formulation 050 (% w/w) | Formulation 056 (% w/w) |
| --- | --- | --- | --- |
| Doxylamine Succinate | 10% | 9% | 9% |
| Pyridoxine Hydrochloride | 9.25% | 8.25% | 8.25% |
| Dimethylsulfoxide | 28% | 30.25% | 32.25% |
| Dipropylene Glycol | 5% | — | — |
| Hexylene Glycol | — | 6% | 6% |
| Glycerine | — | 5% | 3% |
| Ethanol | 5% | — | — |
| Propylene glycol monolaurate type (II) | 4% | 4% | 4% |
| Diethylene Glycol Monoethyl Ether | 18% | 16.25% | 17.25% |
| Water | 17.75% | 16.75% | 12.75% |
| Hydroxypropyl Cellulose HF | — | 2% | 3.5% |
| Carbopol 971p NF | 3% | — | — |
| Carbopol 980 NF | — | 2.5% | — |
| Bentonite | — | — | 4% |

Polymer Matrix with Different Polymers (Using Water as Volatile Solvent)

| Ingredient | Formulation M002 (% w/w) | Formulation M003 (% w/w) | Formulation M004 (% w/w) |
| --- | --- | --- | --- |
| Doxylamine Succinate | 8.5% | 8.5% | 8.5% |
| Pyridoxine Hydrochloride | 8.5% | 8.5% | 8.5% |
| Dimethylsulfoxide | 13.5% | 13% | 13% |
| Diethylene glycol monoethyl ether | 10.5% | 9% | 9% |

-continued

| Ingredient | Formulation M002 (% w/w) | Formulation M003 (% w/w) | Formulation M004 (% w/w) |
|---|---|---|---|
| Propylene Glycol Monolaurate (type II) | 4% | 4% | 4% |
| Glycerine | 26% | 24% | 24% |
| Lactic Acid | — | 4% | 4% |
| Bentonite | — | — | 15% |
| Hydroxypropyl methylcellulose (Methocel E4M Premium CR) | 14% | — | — |
| PVP K30 | 15% | 15% | — |
| Chitosan | — | 14% | 14% |

While the invention has described solvents, enhancers, polymers or gelling agents or thickening agents or similar compounds in detail and with reference to specific examples, it will be apparent to one skilled in the art that various changes, modifications, sub combinations can be made therein without departing from the spirit and scope thereof.

There are a few excipients or chemicals which are common in solvents and enhancers. It is apparent to those skilled in that these excipients can act both as solvents and enhancers at the same time.

Suitable pH adjusting agents for use in the present invention include but are not limited to acids and its derivatives (such as but not limited to hydrochloric acid, phosphoric acid, acetic acid, carboxylic acids, inorganic acids, sulfonic acids, vinylogous carboxylic acids etc), base and its derivatives (such as but not limited to sodium hydroxide, potassium hydroxide, ammonium hydroxide, triethylamine, sodium carbonate, sodium bicarbonate etc), auxiliary pH buffering agents, pH stabilizers and similar compounds (such as but not limited to acetate buffer, citrate buffer, phosphate buffer etc) either alone or in combinations thereof. Preferred pH adjusting agents are acid and base. More preferably hydrochloric acid and sodium hydroxide.

Plasticizers suitable for use in polymer matrix in the present invention include but are not limited to glycerol and its esters, mineral oil, dibutyl sebacate, oleic acid, glycerine, phosphate esters, glycol derivatives, sugar alcohols, sebacic acid esters, azelate, citric acid esters, tartaric acid esters, adipate, phthalic acid esters, triacetin, oleic acid esters and all the plasticizers which can be used in transdermal drug delivery system referred in the book "Handbook of Plasticizers" (George Wypych, 2004, Chem Tec Publishing) either alone or in combinations thereof.

Other than these components, stabilizing agents known to those skilled in the art can be incorporated in the present invention of liquid formulation, semisolid formulation, polymer matrix such as but not limited to discoloring agents, stabilizers, preservatives, oxidizing agents, antioxidants, reducing agents, complexing agents, chelating agents and similar compounds (such as but not limited to sodium metabisulfite, boric acid, citric acid, ascorbic acid, tartaric acid, sorbic acid, ascorbyl palmitate, sodium azide, vitamin E, butylated hydroxyanisole, butylated hydroxytoluene, EDTA, benzyl alcohol, sodium benzoate, butyl paraben, phenol, thiomersal etc) either alone or in combinations thereof.

Furthermore, without any limitation suitable chemicals or excipients for transdermal delivery can be selected from books such as "Remington's the science and practice of pharmacy, $21^{st}$ edition", published by the Wolter's Kluwer Company, PA and book "Handbook of Pharmaceutical Excipients, sixth Edition," published by the Pharmaceutical Press and the American Pharmacists Association, London, USA In the present invention, in addition to Doxylamine and Pyridoxine, minerals and vitamins prescribed in pregnancy can be incorporated either alone or in combinations thereof in pharmaceutical compositions wherein pharmaceutical compositions are liquid formulations, semisolid formulations and polymer matrices. Examples of vitamins and minerals include such as vitamin A, vitamin C, vitamin D3, vitamin E, thiamine, riboflavin, niacin, folic acid, vitamin B12, calcium, iron, zinc, and copper. Further, minerals and vitamins can be incorporated in following forms either alone or in combinations thereof such as pharmaceutically acceptable forms, free base, salt, analog, isomer, amorphous, crystalline, co crystalline, solid solution, prodrug, metabolites, derivatives etc. Furthermore in pharmaceutical compositions Doxylamine, Pyridoxine and above stated mineral and vitamins can be suspended or dissolved or dispersed. Without limiting in scope few exemplary formulations with different vitamins are illustrated in example 8

Example 8

Doxylamine Succinate and Pyridoxine Hydrochloride Formulations with Vitamins

| Ingredients | Formulation 070 (% w/w) | Formulation 071 (% w/w) | Formulation 072 (% w/w) | Formulation 073 (% w/w) | Formulation 074 (% w/w) |
|---|---|---|---|---|---|
| Doxylamine Succinate | 9% | 9% | 9% | 9% | 9% |
| Pyridoxine Hydrochloride | 8.25% | 8.25% | 8.25% | 8.25% | 8.25% |
| Dimethylsulfoxide | 30.25% | 30.25% | 30.25% | 30.25% | 30.25% |
| Hexylene Glycol | 8% | 9.5% | 5% | 8% | 9.5% |
| Thiamine HCl | 2% | — | — | — | — |
| Riboflavin | — | 0.5% | — | — | — |
| Niacinamide | — | — | 5% | — | — |
| Folic Acid | — | — | — | 2% | — |
| Vitamin B12 | — | — | — | — | 0.5% |
| Propylene glycol monolaurate type (II) | 4% | 4% | 4% | 4% | 4% |
| Diethylene Glycol Monoethyl Ether | 17.25% | 17.25% | 17.25% | 17.25% | 17.25% |
| Water | 17.75% | 17.75% | 17.75% | 17.75% | 17.75% |
| Hydroxypropyl Cellulose HF | 3.5% | 3.5% | 3.5% | 3.5% | 3.5% |

While the invention has described vitamins and minerals in detail and with reference to few examples, it will be apparent to one skilled in the art that various changes, modifications, sub combinations can be made therein without departing from the spirit and scope thereof.

Further, a dermal irritation test in rabbits with 7 day exposure was contracted at an independent laboratory, Consumer Product Testing Co. (70 New Dutch Lane, Fairfield, N.J. 07004-2514). The test was conducted with three New Zealand Albino rabbit to evaluate dermal or skin irritation potential of Formulation 046. The rabbit's hair was clipped and two hilltop chambers each containing 0.6 ml of Formulation 046 were topically applied to the dorsal side and kept in place for a period of 7 days. After 7 days, both hilltop chambers were removed and the application sites were scored for edema and erythema as per Draize skin score. The average combined erythema and edema scores per animal per observation was 0.6 on a scale of 0-8 which indicates that Formulation 046 is not irritating.

Figure 2:
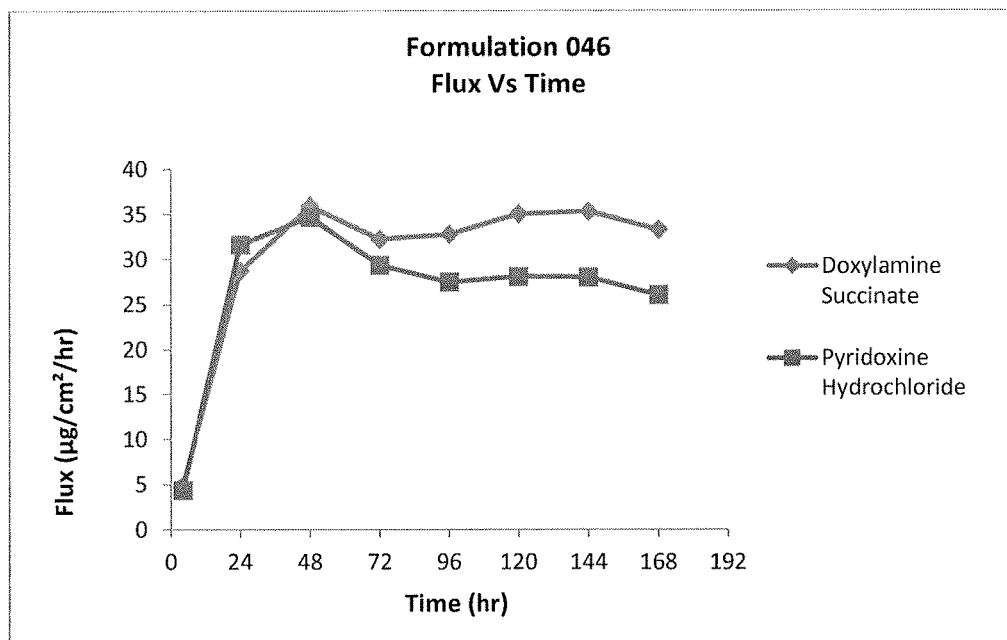
FIG. 2 is a graph of semisolid (gel) Formulation 046 Flux ($\mu g/cm^2/hr$) Vs Time (hr), showing simultaneous in vitro release of Doxylamine Succinate and Pyridoxine Hydrochloride for a period of seven days (168 hr) through human cadaver skin.
Figure 3:
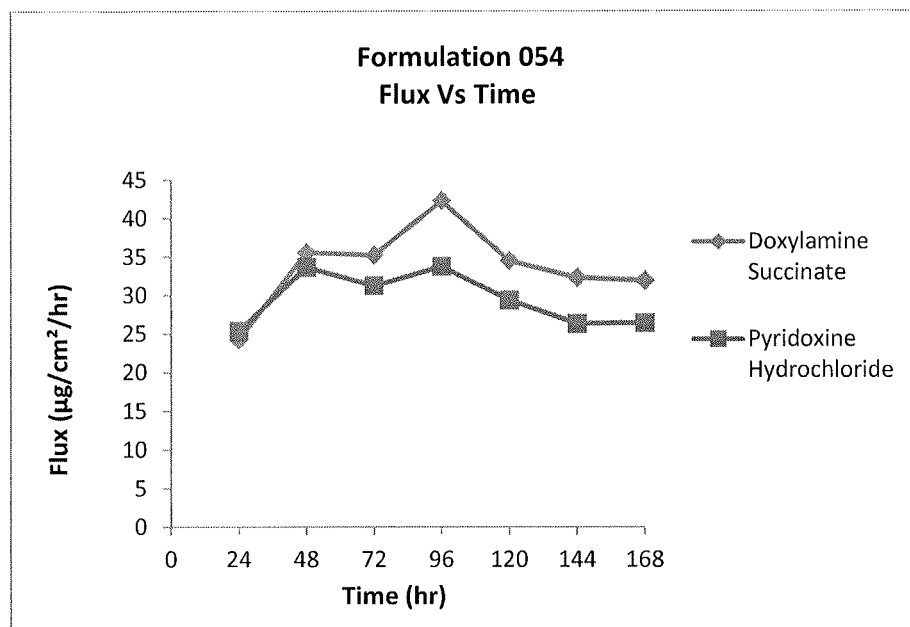
FIG. 3 is a graph of semisolid (gel) Formulation 054 Flux ($\mu g/cm^2/hr$) Vs Time (hr), showing simultaneous in vitro release of Doxylamine Succinate and Pyridoxine Hydrochloride for a period of seven days (168 hr) through human cadaver skin.

The invention will be illustrated with reference to FIGS. 1-3. Formulations are evaluated in vitro with human cadaver skin for the transdermal flux profile of Doxylamine Succinate and Pyridoxine Hydrochloride for a continuous period of 1-3 days and 1-7 days. The average in vitro flux of three days from liquid formulation 016 for Doxylamine Succinate is about 59 $\mu g/cm^2/hr$ and Pyridoxine Hydrochloride is about 61 $\mu g/cm^2/hr$. Surprisingly, the average in vitro flux of Doxylamine Succinate and Pyridoxine Hydrochloride are almost the same which would not be expected even by someone skilled in the art. This further emphasizes that the formulation provides simultaneous transdermal delivery of Doxylamine Succinate and Pyridoxine Hydrochloride.

The average in vitro flux of seven days from semisolid formulation 046 for Doxylamine Succinate is about 34 $\mu g/cm^2/hr$ and Pyridoxine Hydrochloride is about 30 $\mu g/cm^2/hr$. Formulation 046 gave steady state flux of Doxylamine Succinate and Pyridoxine Hydrochloride from 24 hr-168 hr or from day 1-day 7 wherein steady state flux is about 26-36 $\mu g/cm^2/hr$.

Surprisingly, an average in vitro flux and release profile of Doxylamine Succinate and Pyridoxine Hydrochloride are almost the same which further emphasizes that the formulation provides for simultaneous transdermal delivery of Doxylamine Succinate and Pyridoxine Hydrochloride. The average in vitro flux of seven days from semisolid formulation 054 for Doxylamine Succinate is about 34 $\mu g/cm^2/hr$ and Pyridoxine Hydrochloride is about 29 $\mu g/cm^2/hr$. Surprisingly, the average in vitro flux of Doxylamine Succinate and Pyridoxine Hydrochloride are almost the same which further emphasizes that the formulation provides for simultaneous transdermal delivery of Doxylamine Succinate and Pyridoxine Hydrochloride.

From the in vitro Flux results of present invention it can be suggested that formulations can be used for transdermal delivery of therapeutically effective amount of Doxylamine Succinate and Pyridoxine Hydrochloride for treatment of nausea and vomiting from 1-7 days. If required, the flux can be further changed by modifying formulation parameters such as but not limited to Doxylamine Succinate concentration, Pyridoxine Hydrochloride concentration, components of vehicle system such as solvents, enhancers, polymers, gelling agents, thickening agents, pH, patch size etc in accordance with the teachings of the present invention.

Depending upon the severity of symptoms, the duration of topical administration or transdermal delivery of Doxylamine and Pyridoxine from these formulations can be determined by those skilled in the art without any limitation to once in a day, once in two days, once in three days, once in four days, once in five days, once in six days, once in a week, once in 10 days. Those skilled in the art will recognize that the pharmacological effect for the treatment of nausea and vomiting can be obtained by transdermal delivery of Doxylamine and Pyridoxine in different ways such as by topical administration of a pharmaceutical composition comprising both Doxylamine and Pyridoxine or by topical administration of two separate pharmaceutical compositions at the same time wherein, one pharmaceutical composition is comprised of Doxylamine and second pharmaceutical composition is comprised of Pyridoxine.

In one aspect a pharmaceutical composition or formulation comprised of Doxylamine, Pyridoxine and a vehicle system can be applied directly as a topical agent to the skin wherein the formulation is a liquid and/or semisolid and/or polymer matrix. In yet another aspect a pharmaceutical composition or formulation as a liquid and/or semisolid, comprised of Doxylamine, Pyridoxine and vehicle system is incorporated into a transdermal delivery system which is then applied to skin.

In another aspect the pharmaceutical composition or formulation comprised of Doxylamine, Pyridoxine and vehicle system is a polymer matrix wherein the polymer can be adhesive and/or non-adhesive and thus applied directly to the skin. In yet another aspect the pharmaceutical composition or formulation is a polymer matrix, comprised of Doxylamine, Pyridoxine and a vehicle system is incorporated into a transdermal delivery system and then is applied to skin.

In another aspect pharmaceutical composition or formulation comprising Doxylamine and a vehicle system can be applied topically to skin wherein the formulation is a liquid and/or semisolid. In yet another aspect a pharmaceutical composition or formulation is liquid and/or semisolid, comprising Doxylamine and vehicle system is incorporated into a transdermal delivery system and applied directly to the skin.

In yet another aspect pharmaceutical composition or formulation comprising Pyridoxine and vehicle system can be applied topically to skin wherein the formulation is a liquid and/or semisolid. In yet another aspect a pharmaceutical composition or formulation is a liquid and/or semisolid, comprised of Pyridoxine and a vehicle system and is incorporated into a transdermal delivery system and is applied directly to the skin.

A transdermal delivery system can be prepared in different designs. Examples of transdermal delivery systems include without any limitation a reservoir patch, matrix patch, extended release transdermal films, monolithic drug in adhesive patch, multilaminate drug in adhesive patch, membrane modulated system, adhesive dispersion system, matrix dispersion system, micro-reservoir system etc[7]. Design of few transdermal delivery system or patches are disclosed in Remington's the science and practice of pharmacy, 20 edition, published by the Wolter's Kluwer Company, PA.

Furthermore the design of a transdermal delivery system without limiting in scope comprises a pouch formed from an impermeable backing, a rate controlling or porous membrane, if needed, an adhesive peripheral ring, covered by a strippable protective backing, and a detachable protective layer or release liner. The impermeable backing is configured to provide a central volume, which contains a reservoir in the form of a semisolid or liquid formulation (having dissolved and/or suspended Doxylamine and Pyridoxine). Although preferred embodiments of this invention utilize an adhesive peripheral ring outside the path of Doxylamine and Pyridoxine diffusion from the system through the skin, other means for maintaining the system on the skin can be employed. Such means include an in-line adhesive layer; adhesive overlays or other fastening means such as buckles, belts and elastic armbands are also contemplated.

Furthermore design of a transdermal delivery system without limiting in scope comprises Doxylamine and Pyridoxine and vehicle system components which are suspended or solubilized or dispersed in the polymer or adhesive matrix, cover between impermeable backing layer and release liner and/or detachable protective layer. According to the present invention, Doxylamine and Pyridoxine are solubilized or suspended or dispersed in the pressure-sensitive adhesive or polymer matrix, or an extra pressure sensitive adhesive layer may be provided which enables fixation of the transdermal delivery system on the skin. The transdermal delivery system according to this invention can be manufactured in such a manner that polymers containing Doxylamine and Pyridoxine and a vehicle system is coated onto a suitable support, for example to a thermoplastic film provided with a silicone layer, and possibly after evaporation of the solvent components, is covered with a further film which will later constitute the backing layer of transdermal delivery system. The invention also comprises such embodiments where the Doxylamine and Pyridoxine matrix have a two or multi-layered structure. For example, the various matrix layers may contain various constituents. In this case, the matrix layers differ from each other in terms of polymer or pressure sensitive polymers or hot melt polymers composition, Doxylamine and Pyridoxine amount, permeation enhancers, solvents, plasticizers, tackifiers, stabilizers, etc.

The transdermal delivery systems of the present invention can release Doxylamine and Pyridoxine by diffusion. In this mode, the driving force is the difference in Doxylamine and Pyridoxine activity between the transdermal delivery systems and the skin and underlying tissue. The Doxylamine and Pyridoxine, which are dissolved or dispersed or suspended in the vehicle system and/or polymer matrix in the case of the present invention, permeates through the vehicle system or polymer matrix to the skin. The reservoir or matrix system is in direct communication with the skin, which means that it either contacts the skin directly or contacts material interposed between the reservoir or matrix system and that the skin provides a permeation pathway for the Doxylamine, Pyridoxine and enhancers to migrate from the reservoir or matrix system to the skin. The interposed material may be homogenous, heterogeneous, or be composed of multiplicity of distinct layer.

Furthermore the design of a transdermal delivery system without limiting in scope could include a microneedle array that, when applied to the skin prior to the patch of any design, reduces the barrier to diffusion through the skin, enhancing the delivery of Doxylamine and/or Pyridoxine.

Furthermore the design of a transdermal delivery system without limiting in scope could include a hollow microneedle array through which drug flows or a biodegradable microneedle array from which Doxylamine and/or Pyridoxine is released.

While the invention has described a design for a transdermal delivery systems in detail, it will be apparent to one skilled in the art that various changes and modifications can be made therein without departing from the spirit and scope thereof.

In conclusion, the present invention can reduce the dosing frequency of Doxylamine and Pyridoxine to once in day, once in three days, once in seven days as evidenced by simultaneous in vitro release of Doxylamine Succinate and Pyridoxine hydrochloride for a continuous period of seven days.

While the invention has been described in detail and with reference to specific examples thereof, it will be apparent to one skilled in the art that various changes and modifications can be made therein without departing from the spirit and scope thereof.

REFERENCES

1) Einarson T R, Piwko C, Koren G. "Prevalence of nausea and vomiting of pregnancy in the USA: A meta-analysis". J Popul Ther Clin Pharmacol. 2013, 20(2), 163-70.
2) APGO. "Nausea and vomiting of pregnancy. APGO educational series on women's health issues nausea and vomiting of pregnancy". Jespersen & Associates, LLC Boston. 2015
3) Lacroix R, Eason E, Melzack R. "Nausea and vomiting during pregnancy: A prospective study of its frequency, intensity, and patterns of change". Am J Obstet Gynecol. 2000, 182(4), 931-7.
4) Madjunkova S, Maltepe C, Koren G. "The delayed-release combination of Doxylamine and Pyridoxine (DICLEGIS/Diclectin) for the treatment of Nausea and Vomiting of Pregnancy". Paediatr Drugs. 2014, 16(3), 199-211.
5) Niebyl, J R. "Nausea and Vomiting in Pregnancy. N Eng J Med. 2010; 363:1544-50.
6) FDA Label DICLEGIS, www.accessdataida.gov/drugsatfda_docs/label/2013/021876500lbl.pdf, accessed Jul. 4, 2016
7) "Remington's the science and practice of pharmacy, 21$^{st}$ edition", published by the Wolter's Kluwer company, PA.
8) "Handbook of Pharmaceutical Excipients, sixth edition", published by the Pharmaceutical Press and the American Pharmacists Association, London, USA
9) "Percutaneous Penetration Enhancers Chemical Methods in Penetration Enhancement Nanocarriers", published by Springer Heidelberg New York Dordrecht London

What is claimed is:

1. A transdermal pharmaceutical composition as a semisolid formulation wherein the semisolid formulation comprises:
    5-20 wt % Doxylamine Succinate,
    5-20 wt % Pyridoxine Hydrochloride,
    5-45 wt % dimethylsulfoxide,
    1-30 wt % hexylene glycol,
    1-40 wt % diethylene glycol monoethyl ether,
    1-25 wt % propylene glycol monolaurate type (II),
    1-50 wt % water,
    1-10 wt % hydroxypropyl cellulose, and
    hydrochloric acid and/or sodium hydroxide to adjust the pH to between 4-7, wherein the transdermal pharmaceutical composition is in a reservoir patch.

2. A transdermal pharmaceutical composition as a semisolid formulation wherein the semisolid formulation comprises:
    5-20 wt % Doxylamine Succinate,
    5-20 wt % Pyridoxine Hydrochloride,
    5-45 wt % dimethylsulfoxide,
    1-30 wt % hexylene glycol,
    1-40 wt % diethylene glycol monoethyl ether,
    1-25 wt % propylene glycol monolaurate type (II),
    1-30 wt % glycerine,
    1-50 wt % water,
    1-10 wt % hydroxypropyl cellulose, and hydrochloric acid and/or sodium hydroxide to adjust the pH to between 4-7, wherein the transdermal pharmaceutical composition is in a reservoir patch.

3. A transdermal pharmaceutical composition as a semisolid formulation wherein the semisolid formulation comprises:
5-20 wt % Doxylamine Succinate,
5-45 wt % dimethylsulfoxide,
1-30 wt % hexylene glycol,
1-40 wt % diethylene glycol monoethyl ether,
1-25 wt % propylene glycol monolaurate type (II),
1-50 wt % water,
1-10 wt % hydroxypropyl cellulose, and
hydrochloric acid and/or sodium hydroxide to adjust the pH to between 4-7, wherein the transdermal pharmaceutical composition is in a reservoir patch.

4. A transdermal pharmaceutical composition as a semisolid formulation, wherein the semisolid formulation comprises:
5-20 wt % Doxylamine Succinate,
5-45 wt % dimethylsulfoxide,
1-30 wt % hexylene glycol,
1-40 wt % diethylene glycol monoethyl ether,
1-25 wt % propylene glycol monolaurate type (II),
1-30 wt % glycerine,
1-50 wt % water,
1-10 wt % hydroxypropyl cellulose, and
hydrochloric acid and/or sodium hydroxide to adjust the pH to between 4-7, wherein the transdermal pharmaceutical composition is in a reservoir patch.

5. A transdermal pharmaceutical composition as a semisolid formulation wherein the semisolid formulation comprises:
5-20 wt % Doxylamine free base,
5-20 wt % Pyridoxine free base,
5-45 wt % dimethylsulfoxide,
1-30 wt % hexylene glycol,
1-40 wt % diethylene glycol monoethyl ether,
1-25 wt % propylene glycol monolaurate type (II),
1-50 wt % water,
1-10 wt % hydroxypropyl cellulose, and
hydrochloric acid and/or sodium hydroxide to adjust the pH to between 4-7, wherein the transdermal pharmaceutical composition is in a reservoir patch.

6. A transdermal pharmaceutical composition as a semisolid formulation wherein the semisolid formulation comprises:
5-20 wt % Doxylamine free base,
5-20 wt % Pyridoxine free base,
5-45 wt % dimethylsulfoxide,
1-30 wt % hexylene glycol,
1-40 wt % diethylene glycol monoethyl ether,
1-25 wt % propylene glycol monolaurate type (II),
1-30 wt % glycerine,
1-50 wt % water,
1-10 wt % hydroxypropyl cellulose, and
hydrochloric acid and/or sodium hydroxide to adjust the pH to between 4-7, wherein the transdermal pharmaceutical composition is in a reservoir patch.

7. A transdermal pharmaceutical composition as a semisolid formulation wherein the semisolid formulation comprises:
5-20 wt % Doxylamine free base,
5-45 wt % dimethylsulfoxide,
1-30 wt % hexylene glycol,
1-40 wt % diethylene glycol monoethyl ether,
1-25 wt % propylene glycol monolaurate type (II),
1-50 wt % water,
1-10 wt % hydroxypropyl cellulose, and
hydrochloric acid and/or sodium hydroxide to adjust the pH to between 4-7, wherein the transdermal pharmaceutical composition is in a reservoir patch.

8. A transdermal pharmaceutical composition as a semisolid formulation, wherein the semisolid formulation comprises:
5-20 wt % Doxylamine free base,
5-45 wt % dimethylsulfoxide,
1-30 wt % hexylene glycol,
1-40 wt % diethylene glycol monoethyl ether,
1-25 wt % propylene glycol monolaurate type (II),
1-30 wt % glycerine,
1-50 wt % water,
1-10 wt % hydroxypropyl cellulose, and
hydrochloric acid and/or sodium hydroxide to adjust the pH to between 4-7, wherein the transdermal pharmaceutical composition is in a reservoir patch.

9. The transdermal pharmaceutical composition of claim 1, wherein the semisolid formulation comprises:
Doxylamine Succinate about 9.00 wt %,
Pyridoxine HCl about 8.25 wt %,
Dimethyl Sulfoxide, about 30.25 wt %,
Hexylene Glycol about 10.0 wt %,
diethylene glycol monoethyl ether about 17.25 wt %,
Water about 17.75 wt %,
propylene glycol monolaurate type (II) about 4.0 wt %,
hydroxypropyl cellulose about 3.5 wt %, and
hydrochloric acid and/or sodium hydroxide to adjust the pH to between 4-7, wherein the transdermal pharmaceutical composition is in a reservoir patch.

10. The transdermal pharmaceutical composition of claim 5, wherein the semisolid formulation comprises:
Doxylamine Free Base about 9.00 wt %,
Pyridoxine Free Base about 8.25 wt %,
Dimethyl Sulfoxide, about 30.25 wt %,
Hexylene Glycol about 10.0 wt %,
diethylene glycol monoethyl ether about 17.25 wt %,
Water about 17.75 wt %,
propylene glycol monolaurate type (II) about 4.0 wt %,
hydroxypropyl cellulose about 3.5 wt %, and
hydrochloric acid and/or sodium hydroxide to adjust the pH to between 4-7, wherein the transdermal pharmaceutical composition is in a reservoir patch.

* * * * *